(12) United States Patent
Smith et al.

(10) Patent No.: US 7,816,074 B2
(45) Date of Patent: Oct. 19, 2010

(54) $\alpha_4 \beta_2 \delta$ GABA-A RECEPTORS AS A STRATEGY FOR PMS AND ALCOHOLISM

(75) Inventors: Sheryl Smith, Atlantic Beach, NY (US); Keith Williams, Brooklyn, NY (US)

(73) Assignee: The Research Foundation of State University of New York, Albany, NY (US)

( * ) Notice: Subject to any disclaimer, the term of this patent is extended or adjusted under 35 U.S.C. 154(b) by 976 days.

(21) Appl. No.: 10/566,559

(22) PCT Filed: Jul. 30, 2004

(86) PCT No.: PCT/US2004/024981
§ 371 (c)(1), (2), (4) Date: Sep. 18, 2006

(87) PCT Pub. No.: WO2005/011612
PCT Pub. Date: Feb. 10, 2005

(65) Prior Publication Data
US 2007/0081943 A1    Apr. 12, 2007

Related U.S. Application Data

(60) Provisional application No. 60/491,599, filed on Jul. 31, 2003.

(51) Int. Cl.
G01N 33/53    (2006.01)
G01N 33/532    (2006.01)
(52) U.S. Cl. .............. 435/4; 435/7.1; 435/7.2; 435/7.21; 435/7.5; 435/7.92
(58) Field of Classification Search .............. None
See application file for complete search history.

(56) References Cited

U.S. PATENT DOCUMENTS 5,189,064 A    2/1993    Blum et al.

2002/0115611 A1    8/2002    Tallman et al.
2003/0138776 A1    7/2003    Goldman et al.

FOREIGN PATENT DOCUMENTS

WO    WO 96/10637    *    4/1996

OTHER PUBLICATIONS

Borghese CM et al. Studies of ethanol actions on recombinant delta-containing GABA-A receptors yield contradictory results. Alcohol, May 2007; 41(3):155-162.*
Feldman RS et al. Principles of Neuropsychopharmacology. 1997, Sinauer Associates, Inc., Publishers; Sunderland, MA; pp. 430-433.*
Gault LM et al. NMDA receptor stimulation selectively initiates GABA-A receptor delta subunit mRNA expression in cultured rat cerebellar granule neurons. J. Neurochem. 1998; 70:1907-1915.*
Smith S et al. a4b2d GABAA receptors exhibit a unique sensitivity to low concentrations of alcohol: Behavioral correlations in female rats. Meeting abstract from the 11th Congress of the International Society for Biomedical Research on Alcoholism. Alcoholism Clinical Exp Res. May 2002; 26(5 Suppl):16A, Abstract #65.*
Sundstrom-Poromaa et al., (Jul. 2002), "Hormonally Regulated $\alpha_4\beta_2\delta$ GABA$_A$ Receptors Are A Alcohol", *Nature Neuroscience* 5:8 721-722.

* cited by examiner

*Primary Examiner*—Bridget E Bunner
*Assistant Examiner*—Christina Borgeest
(74) *Attorney, Agent, or Firm*—Dilworth & Barrese, LLP

(57) ABSTRACT

The present invention is directed to a screening mechanism for identifying members of the general population at increased risk for alcoholism and premenstrual syndrome. The screening mechanisms may be used to measure the expression of the $\alpha_4\beta_2\delta$ GABA$_A$ receptors, in order to identify members of the general population as having an increased sensitivity to lower concentrations alcohol coupled with a decrease sensitivity to higher concentrations of alcohol, a scenario frequently found in patients suffering from alcoholism and premenstrual anxiety. Methods of screening for drugs which decrease expression of the $\alpha_4\beta_2\delta$ subunit of GABA$_A$ are also provided.

1 Claim, 13 Drawing Sheets

FIGURES 9 A-D
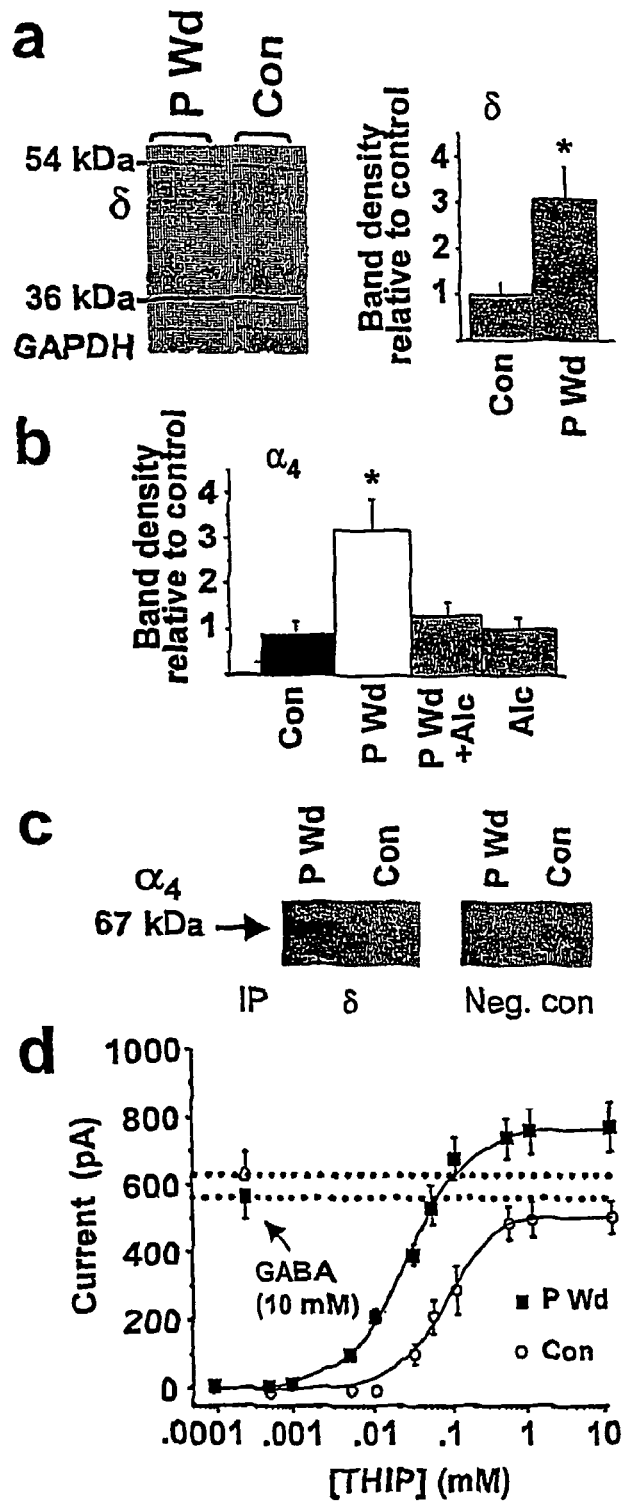

# $\alpha_4 \beta_2 \delta$GABA-A RECEPTORS AS A STRATEGY FOR PMS AND ALCOHOLISM

CROSS REFERENCE TO RELATED APPLICATIONS

This application claims priority to U.S. Provisional Application Ser. No. 60/491,599 filed Jul. 31, 2003, which application is incorporated by reference herein.

BACKGROUND OF THE INVENTION

Alcohol is an addictive recreational drug that reduces anxiety at low doses and causes sedation at high doses (1). These effects are similar to those of drugs that enhance the function of gamma-amino butyric acid sub A. receptor, referred to herein as $GABA_A$ receptor, which gate the Cl⁻ currents that mediate most inhibitory neurotransmission in the brain. Gamma-amino butyric acid (GABA) is a major inhibitory neurotransmitter in the central nervous system. It mediates fast synaptic inhibition by opening the chloride channel intrinsic to the GABA (A) receptor. Acutely high doses of alcohol potentiate GABA-gated currents (1) at both native (1) and recombinant $GABA_A$ receptors (42), and chronically alter $GABA_A$ receptor expression (34). Low doses of alcohol have not been shown to directly modulate recombinant $GABA_A$ receptors (1), although there is indirect evidence for such effects at native receptors (6, 7, 29, 76).

It has been suggested that discrepancies between the alcohol sensitivity of native and recombinant receptors may be due to their subunit composition (64). Therefore there is a need to investigate the effects of low concentrations of alcohol on different subtypes of $GABA_A$ receptors.

Recently, a novel subunit combination of the $GABA_A$ receptor, $\alpha_4\beta_2\delta$, was identified (67), which is potentiated by very low concentrations of ethanol (1-3 mM), assessed using two electrode voltage clamp procedures and heterologous expression in oocytes. However, higher concentrations of ethanol (>10 mM) were ineffective in this regard, resulting in an "inverted U" concentration-response relationship. Because other subtypes were unresponsive to this low concentration of ethanol, including $\alpha_4\beta_2\gamma_2$ subunits of the $GABA_A$ receptor, this suggests that $\alpha_4\beta\delta$ subunits of the $GABA_A$ receptor possess a unique sensitivity to ethanol (67, 76).

Ethanol is known to exert behavioral (34) and electrophysiological (58) effects at relatively low concentrations. Low concentrations of ethanol can exert both postsynaptic and presynaptic effects in hippocampus and amygdala (8, 58, 76). This presynaptic effect of ethanol is enhanced when $GABA_B$ receptors are blocked (76), suggesting an effect of the drug on transmitter release, while effects on GABAergic transmission in amygdala are mediated via CRF1 receptors (54). Behavioral studies indicate that $GABA_A$ receptor antagonists/negative modulators can decrease ethanol consumption (32, 40), and ethanol can substitute for other GABA-modulatory drugs in drug discrimination tasks (18). Despite this evidence at native receptors, ethanol modulation of most recombinant $GABA_A$ receptor subtypes (50, 27), NMDA receptors (43), and glycine receptors (50) require comparatively high concentrations of the drug. In fact, the anesthetic effect of ethanol requires identified residues on the M2 region of the $GABA_A$ receptor (50). In contrast, the only recombinant receptor thus far identified as responsive to low concentrations of ethanol is the $\alpha_4\beta\delta$ subunit combination of the $GABA_A$ receptor.

The $\alpha_4\beta\delta$ subunits of the $GABA_A$ receptor have very low expression in most areas of the central nervous system (53, 81). The $\alpha_4\beta\delta$ subunits of the $GABA_A$ receptor also exhibit a distinctive response to GABA agonists, producing a greater maximum current in response to 4,5,6,7-tetrahydroisoxazolo[5,4-c]pyridin-3-ol (THIP or gaboxadol), a GABA partial agonist, compared to the maximum current gated by GABA (6), suggesting that 4,5,6,7-tetrahydroisoxazolo[5,4-c]pyridin-3-ol is a full agonist at $\alpha_4\beta\delta$ subunits of the $GABA_A$ receptor. A similar increase in the ratio of maximum 4,5,6,7-tetrahydroisoxazolo[5,4-c]pyridin-3-ol response to maximum GABA response was noted in isolated hippocampal neurons after progesterone withdrawal (67, 25), consistent with increased expression of $\alpha_4\beta\delta$ subunits of the $GABA_A$ receptor at this time. Coexpression of $\alpha_4$ and $\delta$ subunits of the $GABA_A$ receptor was also determined directly in hippocampus using co-immunoprecipitation techniques (67).

Under these conditions of increased expression of $\alpha_4\beta\delta$ subunits of the $GABA_A$ receptor after progesterone withdrawal, GABA-gated current recorded from isolated hippocampal neurons was also potentiated by 1-3 mM, but not higher (>10 mM), concentrations of ethanol (67). Suppression of $\alpha_4$ expression prevented the response to 1-3 mM ethanol after P withdrawal, further suggesting that $\alpha_4\beta\delta$ subunits of the $GABA_A$ receptor possess a unique sensitivity to ethanol. Interestingly, ethanol withdrawal also increases expression of the $\alpha_4$ subunit of the $GABA_A$ receptor (44, 14) but decreases expression of the $\delta$ subunit of the $GABA_A$ receptor (7), an effect correlated with a decrease in response to ethanol.

Therefore, there is a need to understand the relationship between the $\alpha_4\beta\delta$ $GABA_A$ receptor and increased sensitivity to alcohol in order to provide a mechanism for identifying and treating members of the general population at increased risk for alcoholism and premenstrual anxiety, also known as premenstrual syndrome, herein designated PMS.

SUMMARY OF THE INVENTION

The present invention provides methods and compositions for determining whether a subject is at increased risk for alcoholism or premenstrual anxiety. In one aspect of the invention, there is provided a method comprising the steps of: (a) administering to a subject a therapeutically effective amount of a $GABA_A$ receptor modulator and determining whether the subject is sensitive or insensitive to such $GABA_A$ receptor modulator; (b) subsequently administering a therapeutically effective amount of a $GABA_A$ receptor agonist and determining whether the subject is sensitive or insensitive to such $GABA_A$ agonist; and (c) correlating a decreased sensitivity to a $GABA_A$ receptor modulator and an increased sensitivity to a $GABA_A$ agonist with an increased risk of alcoholism or premenstrual anxiety in the subject.

In another aspect of the present invention, there is provided a method of screening for a drug which decreases expression of the $\alpha_4\beta_2\delta$ subunit of $GABA_A$, comprising the steps of: (a) isolating and culturing neurons; (b) applying a drug to the cultured neurons; (c) measuring the level of $\delta$ subunit of $GABA_A$ from the treated neurons of step (b); (d) determining whether the drug applied in step (b) decreases expression of the $\delta$ subunit of $GABA_A$ receptors; and (e) correlating a decrease in expression of the $\delta$ subunit of $GABA_A$ receptors found in the treated neurons of step (b) when compared to a control neuron culture having no drug application, with the identification of a drug which decreases expression of $\alpha_4\beta_2\delta$ $GABA_A$ receptors.

The present invention also provides an additional method of screening for a drug which decreases expression of the $\alpha_4\beta_2\delta$ subunit of $GABA_A$ receptor. The method comprises the steps of: (a) expressing $\alpha_4\beta_2\delta$ GABA$_A$ receptors ineukaryotic cells (b) applying a drug to the eukaryotic cells of (a); (c) measuring the level of $\delta$ subunit of GABA$_A$ from the treated eukaryotic cells of step (b); (d) determining whether the drug applied in step (b) decreases expression of the $\delta$ subunit of GABA$_A$ receptors; and (e) correlating a decrease in expression of the $\delta$ subunit of GABA$_A$ receptors found in the treated eukaryotic cells of step (b) when compared to a control eukaryotic cell population having no drug application, with the identification of a drug which decreases expression of $\alpha_4\beta_2\delta$ GABA$_A$ receptors.

The present invention provides a drug, which blocks $\alpha_4\beta_2\delta$ GABA$_A$ receptors and a method of treating a subject at risk for alcoholism, comprising administering a therapeutically effective amount of a drug which decreases or blocks the expression of $\alpha_4\beta_2\delta$ GABA$_A$ receptors.

Also provided by the present invention is a method for identifying a drug, which blocks $\alpha_4\beta_2\delta$ GABA$_A$ receptors. The method comprising the steps of: (a) isolating and culturing neurons; (b) applying a drug to the cultured neurons of (a); (c) measuring GABA$_A$ gated currents at $\alpha_4\beta_2\delta$ GABA$_A$ receptors in the treated neurons of (b); and (d) correlating a decrease in GABA$_A$-gated currents recorded at $\alpha_4\beta_2\delta$ GABA$_A$ receptors when compared to a control culture with no drug application, with the identification of a drug which blocks $\alpha_4\beta_2\delta$ GABA$_A$ receptors.

In yet another embodiment, the present invention provides an additional method for identifying a drug, which blocks $\alpha_4\beta_2\delta$ GABA$_A$ receptors. The method comprises the steps of: (a) expressing $\alpha_4\beta_2\delta$ GABA$_A$ receptors in eukaryotic cells; (b) applying a drug to the eukaryotic cells of (a); (c) measuring GABA$_A$ gated currents at $\alpha_4\beta_2\delta$ GABA$_A$ receptors in the treated eukaryotic cells of (b); and (d) correlating a decrease in GABA$_A$-gated currents recorded at $\alpha_4\beta_2\delta$ GABA$_A$ receptors when compared to a eukaryotic cell population having no drug application, with the identification of a drug which blocks $\alpha_4\beta_2\delta$ GABA$_A$ receptors.

BRIEF DESCRIPTION OF THE DRAWINGS

FIG. 9A is a representative western blot showing the effects of progesterone withdrawal (PWd) on $\alpha_4\beta\delta$ GABA$_A$ receptors as compared to controls (CON). FIG. 9B graphically depicts the same. FIG. 9C is a representative western blot of the co-assembly of $\alpha_4$ and $\delta$ GABA$_A$ receptor showing the effects of PWd as compared to controls. FIG. 9D graphically depicts the maximum current produced by THIP compared to that of GABA after PWd.

DETAILED DESCRIPTION OF THE INVENTION

Figure 1:
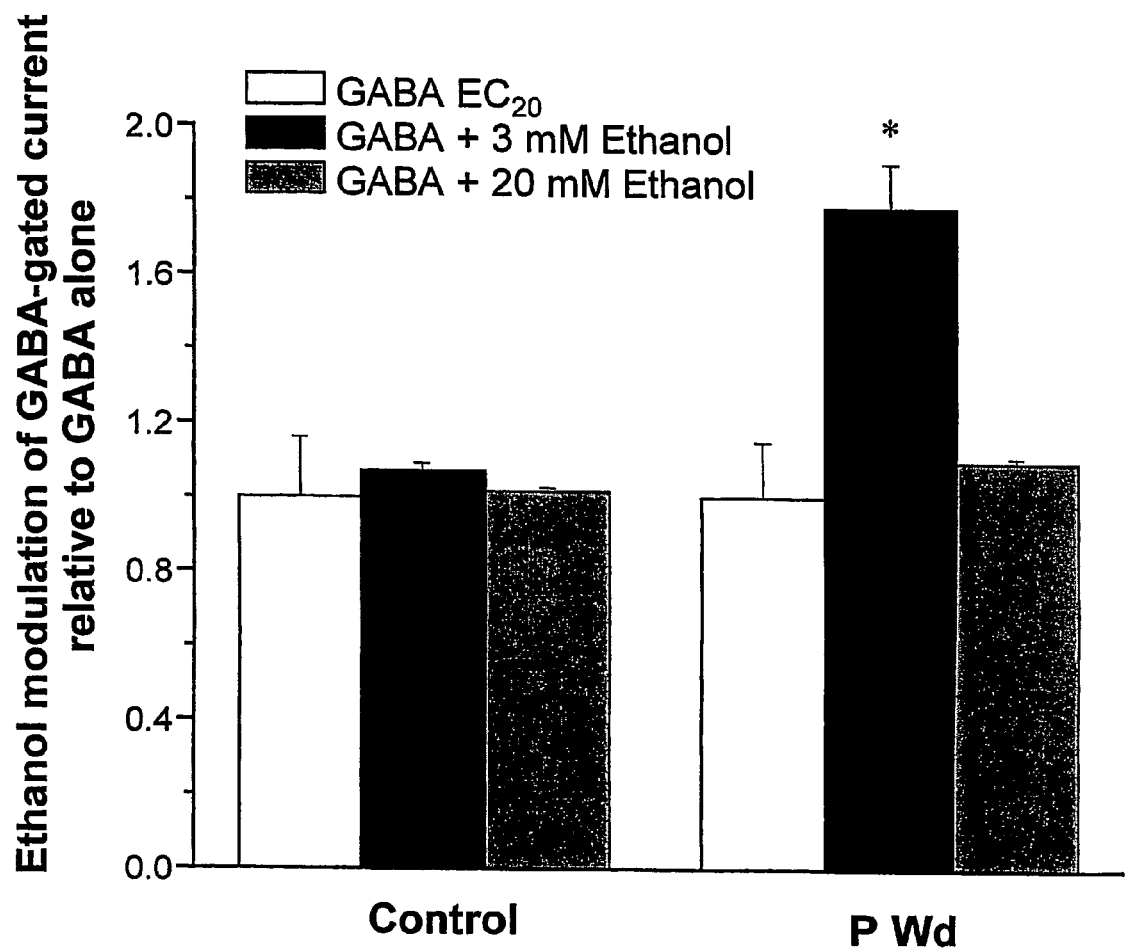
FIG. 1 graphically illustrates ethanol modulation of GABA-gated current relative to GABA alone.

In accordance with the present invention, it has been surprisingly found that very low concentrations of alcohol, e.g., as little as 1 mM ethanol, selectively increase GABA-gated currents at $\alpha_4\beta_2\delta$ receptors by 45±11% (P<0.05). Also in accordance with the present invention, the $\alpha_4\beta_2\delta$ GABA$_A$ receptor isoform is unique in its responsiveness (sensitivity) to such low concentrations of ethanol. Thus, members of the general population who have increased expression of the $\alpha_4\beta_2\delta$ GABA$_A$ receptor isoform are likely to have an increased sensitivity to lower concentrations of alcohol coupled with a decreased sensitivity to higher concentrations of alcohol, a scenario frequently found in patients suffering from alcoholism and PMS.

Based on these findings, the present invention provides a screening mechanism for identifying members of the general population at increased risk for alcoholism.

The method comprises the steps of:

(a) administering to a subject a therapeutically effective amount of a GABA$_A$ receptor modulator and determining whether the subject is sensitive or insensitive to such GABA$_A$ receptor modulator; (b) subsequently administering a therapeutically effective amount of a GABA$_A$ receptor agonist and determining whether the subject is sensitive or insensitive to such GABA$_A$ agonist; and (c) correlating a decreased sensitivity to a GABA$_A$ receptor modulator and an increased sensitivity to a GABA$_A$ agonist with an increased risk of alcoholism and/or PMS in the subject.

An example of GABA$_A$ receptor modulator is a benzodiazepine. Examples of benzodiazepine include but are not limited to Valium (diazepam), Activan (lorazepam), Midazolam, Zolpidem or Flunitrazepam. Additional examples of GABA$_A$ receptor modulators include neurosteroids, such as allopregnanolone or 3$\alpha$,5$\alpha$-THP, benzodiazepine antagonists, such as flumazenil, benzodizepine inverse agonists, such as DMCM (methyl-6,7-dimethoxy-4-ethyl-beta-carboline-3-carboxylate), barbiturates, such as pentobarbital, anesthetics, such as propofol, volatile anesthetics, such as halothane and ethanol. Dosages may vary and may include for example a dose range of about 1 to about 20 mg/kg.

An example of a GABA$_A$ receptor agonist includes but is not limited to gaboxadol, also known as THIP (4,5,6,7-tetrahydroisoxazolo[5,4-c]pyridin-3-ol) and may be administered in the range of from about 1 to about 3 mg/kg. Additional examples of GABA$_A$ receptor agonists include muscimol, beta-alanine, taurine, THIP (gaboxadol), isoguvacine, trans-4-aminocrotonic acid, TACA, (z)-3-[(aminoiminomethyl)thio-2-propenoic acid, ZAPA, and piperidine-4-sulfonic acid (P-4S).

Also provided by the present invention is a method of screening for a drug, which decreases expression of the $\alpha_4\beta_2\delta$ subunit of the GABA$_A$ receptor Drugs identified by this method are useful for treatment of alcoholism. The method comprises the steps of: (a) isolating and culturing neurons; (b) applying a drug to the cultured neurons; (c) measuring the level of $\delta$ subunit of GABA$_A$ from the treated neurons of step (b); (d) determining whether the drug applied in step (b)

decreases expression of the δ subunit of $GABA_A$ receptors; and (e) correlating a decrease in expression of the δ subunit of $GABA_A$ receptors found in the treated neurons of step (b) when compared to a control neuron culture having no drug application, with the identification of a drug which decreases expression of $\alpha_4\beta_2\delta$ $GABA_A$ receptors. Methods for culturing neurons are well known in the art as described e.g., in "Heterogeneity of GABA(A) receptor-mediated responses in the human IMR-32 neurobalstoma cell line." *J. Neuroscience Res.* 60(4): 504-10, May 15, 2000, which article is incorporated by reference herein as if fully set forth. Examples of neurons suitable for use in the methods of the present invention include but are not limited to IMR-32 neurobalstoma, slice cultured neurons, neurobalstoma cell lines such as IMR-32 NTZ and other cultured rodent neurons.

Alternatively, a method of screening for a drug which decreases expression of the $\alpha_4\beta_2\delta$ subunit of the $GABA_A$ receptor comprises the steps of: (a) expressing $\alpha_4\beta_2\delta$ $GABA_A$ receptors in eucaryotic cells (b) applying a drug to the eukaryotic cells of (a); (c) measuring the level of δ subunit of $GABA_A$ from the treated eukaryotic cells of step (b); (d) determining whether the drug applied in step (b) decreases expression of the δ subunit of $GABA_A$ receptors; and (e) correlating a decrease in expression of $\alpha_4\beta_2\delta$ $GABA_A$ receptors found in the treated eukaryotic cells of step (b) when compared to a control eukaryotic cell population having no drug application, with the identification of a drug which decreases expression of $\alpha_4\beta_2\delta$ $GABA_A$ receptors.

Examples of eukaryotic cells suitable for use in the methods of the present invention include but are not limited to *Xenopus laevis* oocytes, Chinese hamster ovaries (CHO) cells, mouse fibroblast L929 cells, mouse L(-tk) fibroblast cell line, human embryonic kidney cells (HEK-293 cells) green monkey kidney cells, COS cells, or variants thereof.

Levels of the δ subunit of $GABA_A$ may be measured e.g., using an immunological detection method such as a Western blot procedure or the pharmacological tests described above. An antibody for the δ subunit of $GABA_A$ is readily available (56).

Expression of $\alpha_4\beta_2\delta$ $GABA_A$ receptors in eukaryotic cells may be performed using methods well known in the art. For example, the nucleotide sequences for the $\alpha_4\beta_2\delta$ $GABA_A$ receptor subunits may be subcloned into an appropriate expression vehicle such as a vector. There are various combinations which may be used to express such $GABA_A$ receptor subunits. For example, several expression vectors may be employed to express each subunit sequence separately. Alternatively, two or more subunit sequences may be expressed in the same expression vector.

Nucleotide sequences for the various $GABA_A$ receptor subunits, appropriate for use in an expression vector, are known and widely available. For example, mouse $\alpha_4$ (37), human $\alpha_4$ (52), rat $\beta_2$ (83), mouse $\beta_2$ (36), human δ (12) and rat δ (63) may be used.

Expression of the different $GABA_A$ receptor subunits sequence may be achieved by operably linking a promoter sequence to a receptor coding sequence using well known methods. Examples of promoters which function in eukaryotic cells and which may be used in the methods of the present invention include but are not limited to T7, CMV, and SV40. Methods of constructing expression vectors using such promoters are well known (59). Commercially available vectors may include, for example, PCDM8, pCDNA3.1 or pGHEMHE (Invitrogen, Carlsbad, Calif.).

Transfection of eukaryotic cells with nucleotide sequences for the $\alpha_4\beta_2\delta$ $GABA_A$ receptor subunits may be performed using various well-known methodologies such as calcium phosphate, DEAE dextran, lipofection, electroporation, and injection. In order to express the $\alpha_4\beta_2\delta$ $GABA_A$ receptor subunits in a eukaryotic cell, the expression vector may be introduced into the cell using the transfection methods described above. Alternatively, mRNA transcripts, or cRNA encoding the receptor subunits may be introduced into the eukaryotic cells. For example, oocytes may be injected with receptor subunit cRNAs. A range of from about 1 t about 100 ng of each receptor subunit sequence per 35 mm diameter dish of confluent cells may be used. Preferably, a range of from about 2 to about 20 ng of each receptor subunit sequence per 35 mm diameter dish of confluent cells is used In still another embodiment of the present invention, there is provided a method of screening for a drug which blocks $\alpha_4\beta_2\delta$ $GABA_A$ receptors. Drugs identified by this method are useful for treatment of alcoholism. The method comprises the steps of: (a) isolating and culturing neurons; (b) applying a drug to the cultured neurons of (a); (c) measuring $GABA_A$ gated currents at $\alpha_4\beta_2\delta$ $GABA_A$ receptors in the treated neurons of (b); and (d) correlating a decrease in $GABA_A$-gated currents recorded at $\alpha_4\beta_2\delta$ $GABA_A$ receptors when compared to a control culture with no drug application, with the identification of a drug which blocks $\alpha_4\beta_2\delta$ $GABA_A$ receptors. Alternatively, the method comprises the steps of: (a) expressing $\alpha_4\beta_2\delta$ $GABA_A$ receptors in eukaryotic cells; (b) applying a drug to the eukaryotic cells of (a); (c) measuring $GABA_A$ gated currents at $\alpha_4\beta_2\delta$ $GABA_A$ receptors in the treated eukaryotic cells of (b); and (d) correlating a decrease in $GABA_A$-gated currents recorded at $\alpha_4\beta_2\delta$ $GABA_A$ receptors when compared to a eukaryotic cell population having no drug application, with the identification of a drug which blocks $\alpha_4\beta_2\delta$ $GABA_A$ receptors.

Also provided by the present invention are methods of treating a patient at risk for, or suffering from, alcoholism. The methods comprise administering to the patient a therapeutically effective amount of a drug which decreases expression of, and/or blocks $\alpha_4\beta_2\delta$ $GABA_A$ receptors.

The following examples further describe the invention and are not meant in any way to limit the scope thereof.

Example I

Materials and Methods

Materials

Adult, female Long Evans rats (200-250 grams at the time of testing) were used in the following example. Animals were housed in pairs under controlled conditions (14:10 light:dark cycle, 24° C.) with free access to food and water. Progesterone (P, Sigma, crystalline)-filled capsules of silicone tubing (Nalgene Co. 1/16"×1/8" o.d., 10 mm/100 g body weight) were implanted subcutaneously in the lower back after induction of halothane anesthesia (3-6% in $O_2$, 1 liter/minutes) in the experimental animals. This paradigm has been shown to result in hippocampal and circulating levels of 3α,5α-THP and circulating levels of P in the physiological range (51), and halts estrous cyclicity until 8 hours after removal of the capsule. Capsules were removed under halothane anesthesia after a 21-day P administration period, and animals tested 24 hours after the last injection ("P withdrawal"). Control animals were tested on the day of diestrus, also referred to as diestrus controls, a low hormone state, as determined by vaginal lavage. This stage results in α4 levels similar to chronic P treatment (64). In addition, separate control animals, also referred to as sham controls, were implanted with empty capsules and tested with selected high or low doses of ethanol in the ASR paradigm or elevated plus maze 24 hours after implant removal. All animals were tested between 0730 and 1100 hour. Euthanasia was either by decapitation in the electrophysiology experiments or $CO_2$ inhalation for the behavioral experiments following the indicated protocols. Both care and use of, as well as all procedures involving animals have been approved by the SUNY Downstate Medical Center Institutional Animal Care and Use Committee. In addition, all procedures were performed in accordance with the guidelines of the Institutional Care and Use Committee of the National Institute on Drug Abuse, National Institutes of Health, and the *Guide for the Care and Use of Laboratory Animals* (33).

Statistical Analysis

Average values for ethanol-induced changes in peak GABA-gated current and the ASR were evaluated across drug-treatment groups by one-way analysis of variance (ANOVA) with a post-hoc Tukey's test. Data from the plus maze were analyzed in an ANOVA followed by post hoc t-tests (Fisher's PLSD). A progesterone value <0.05 was used as an indication of statistical significance.

Patch Clamp Electrophysiology: Methods

Pyramidal neurons were acutely dissociated from CA1 hippocampus and GABA-gated Cl⁻ currents analyzed using whole cell patch clamp procedures as previously described (67). Briefly, tissue was digested at 32° C. for 50-60 minutes under 100% $O_2$ in PIPES-buffered saline containing (in mM): NaCl 120, KCl 5, $CaCl_2$ 1, $MgCl_2$ 1, D-glucose 25, PIPES 20 and trypsin (type XI, sigma) 0.8 mg/ml, pH 7.0. After 1 hour of enzyme-free incubation at room temperature, tissue was dissociated by trituration in 1 ml of 20 mM HEPES-buffered DMEM which was replaced by recording medium after transfer to the recording chamber. GABA-gated currents were recorded at room temperature (20-25° C.) at a holding potential of −50 mV in a bath containing (in mM): NaCl 120, CsCl 5, $CaCl_2$ 2, $MgCl_2$ 1, TEA Cl 15, 4-aminopyridine 5, HEPES 10 and glucose 25, pH 7.4, 320 mOsm/kg $H_2O$. The pipette solution contained (in mM): N-methyl-D-glucamine chloride 120, $Cs_4$BAPTA 5 and Mg-ATP 5. The ATP regeneration system Tris phosphocreatine (20 mM) and creatine kinase were added to minimize GABA rundown. All drugs were obtained from Sigma Chemical Co, (St. Louis, Mo.), except for BAPTA (Calbiochem, San, Diego, Calif.).

For the ethanol administration studies, drug delivery was accomplished with a superfusion system positioned within 50-100 µM of the cell, which yielded approximate 40-100 ms exposure times. Ethanol (3 or 20 mM) was applied concomitant with GABA ($EC_{20}$=10 µM). Peak currents were calculated for all drug concentrations as relative to the current gated by 10 µM GABA alone using the equation: ([peak current: GABA+ETOH]−[peak current: GABA alone])/ [peak current: GABA alone]. Currents were recorded using an Axopatch 1D amplifier (Axon Instruments) filtered at 2 kHz (four-pole Bessel filter) and detected at 500 Hz (pClamp 5.1).

Results

Ethanol Modulation of GABA-Gated Current

After progesterone withdrawal, GABA-gated responses of acutely isolated CA1 hippocampal pyramidal cells were potentiated by a mean 75±10% (P<0.01) with a 3 mM concentration of ethanol (FIG. 1). In contrast, a higher 20 mM concentration of the drug was ineffective in potentiating this parameter, whereas neither concentration produced an effect on GABA responses in cells from control animals. These results confirm findings described in an earlier report (67), and indicate that progesterone withdrawal produces a state where $GABA_A$ receptors are more responsive to very low, but not higher, concentrations of ethanol.

Acoustic Startle Response (ASR) Methods

Animals were tested in a stabilimeter device (SR-Lab Startle Response System, San Diego Instruments, Inc., San Diego, Calif.) that permits vertical movement of a Plexiglas platform contained within a lit, well-ventilated sound-attenuating chamber (26). The amplitude of movement is detected by a piezoelectric device with a voltage output proportional to platform displacement. The analog output of the accelerometer is then amplified and digitized before computer analysis. Five minutes after i.p. administration of 10% ethanol (0.05-1.6 g/kg) or saline vehicle (1.5 ml volume) or 25 minutes after 4,5,6,7-tetrahydroisoxazolo[5,4-c]pyridin-3-ol injection (3 mg/kg, i.p.), animals were placed in the chamber for a 5 minutes acclimation period. The drug latencies were previously established in this laboratory (25, 67) and others (34) as optimal for the anxiolytic effects of these two drugs, which have distinct pharmacokinetics. Four acoustic stimuli (116 dB, 40 ms duration) were then presented at random intervals once every 10-15 seconds via a white-noise generator through speakers positioned on either side of the cage. The 40 ms 116 dB acoustic stimulus has previously been demonstrated in a paradigm (26) as the minimum effective stimulus to produce a robust startle response in all animals. For each acoustic stimulus, the amplitude and integrated response (amplitude and duration) were determined and normalized to the weight of the animal. Values for the integrated response after administration of each dose of ethanol or 4,5,6,7-tetrahydroisoxazolo[5,4-c]pyridin-3-ol were averaged and expressed as a fraction of the saline control average for the indicated treatment (progesterone withdrawal versus control) group in order to minimize variability between groups. This paradigm has been used to demonstrate the anxiolytic effects of low doses of ethanol in ethanol-preferring rats (P rats, 34). It is also routinely used to assess behavioral excitability after withdrawal from BDZs and ethanol (73).

Results

Effects of Ethanol on the Acoustic Startle Response (ASR)

Figure 2A:
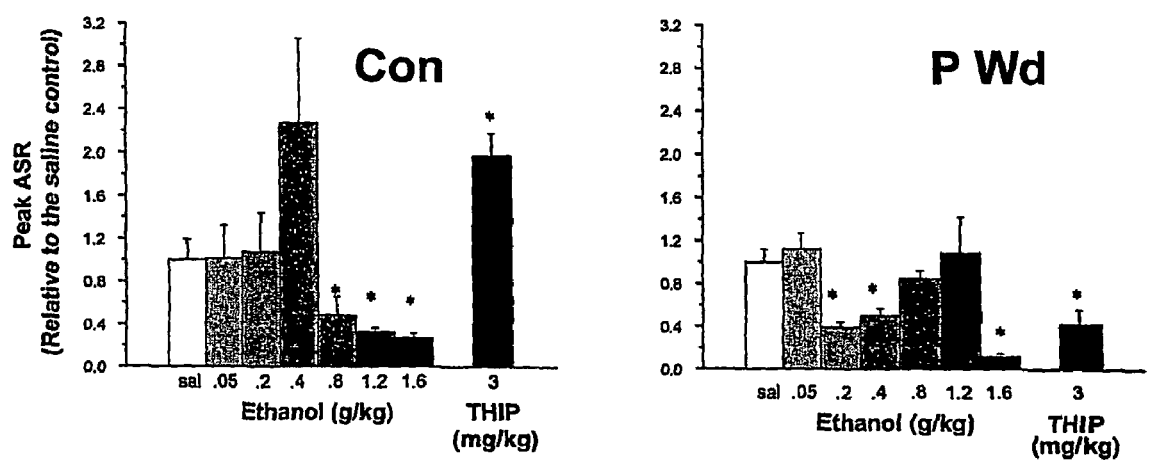
FIGS. 2A-2B illustrate the effect of ethanol on the peak acoustic startle response after progesterone withdrawal.

In order to compare the concentration dependence of ethanol effects in a behavioral paradigm, ethanol was tested across a concentration range (0.05-1.6 g/kg, i.p.) for its effect in modulating the ASR, a measure of behavioral excitability, which is increased after P withdrawal (26). To this end, animals were injected with ethanol or saline vehicle 5 minutes before placement in an acoustically isolated startle chamber. After an additional 5 minutes acclimation period, the startle responses to four 116 dB acoustic stimuli were averaged and adjusted for the weight of the animal. Both average peak and integrated startle responses were significantly (P<0.05) attenuated by about 70% with very low (0.2-0.4 g/kg) doses of ethanol after P withdrawal, an effect not observed in diestrous control animals or in sham control animals (FIGS. 2A, B). Higher doses (0.8-1.2 g/kg) of the drug, however, were ineffective in altering the ASR in P withdrawn animals, but significantly decreased the ASR in both control groups (P<0.05). The highest dose tested (1.6 g/kg) decreased the ASR in both P withdrawal and diestrous control animals to a similar degree, whereas the lowest dose tested (0.05 g/kg) was equally ineffective in these two groups. Thus, the concentration dependence of the anxiolytic effects of ethanol on GABA-gated current after P withdrawal are such that very low doses are highly effective, but higher doses are ineffective in reducing the ASR.

Capsule implantation was not responsible for the altered response to ethanol, as both diestrous (unimplanted) controls and sham controls (implanted with an empty capsule) reacted in a similar manner, with 0.8 g/kg effective, but 0.2 g/kg ineffective in decreasing the peak ASR (FIGS. 2A, B). The two control groups also exhibited similar levels of anxiety, assessed by nearly identical mean ASR scores. In contrast, the P withdrawn animals had significantly higher (P<0.01) baseline ASR scores following saline injection compared to the control groups (integrated ASR, 1165±120, P Wd vs. 485.4±114, diestrous control, 433.5±56, sham control).

Figure 2B:
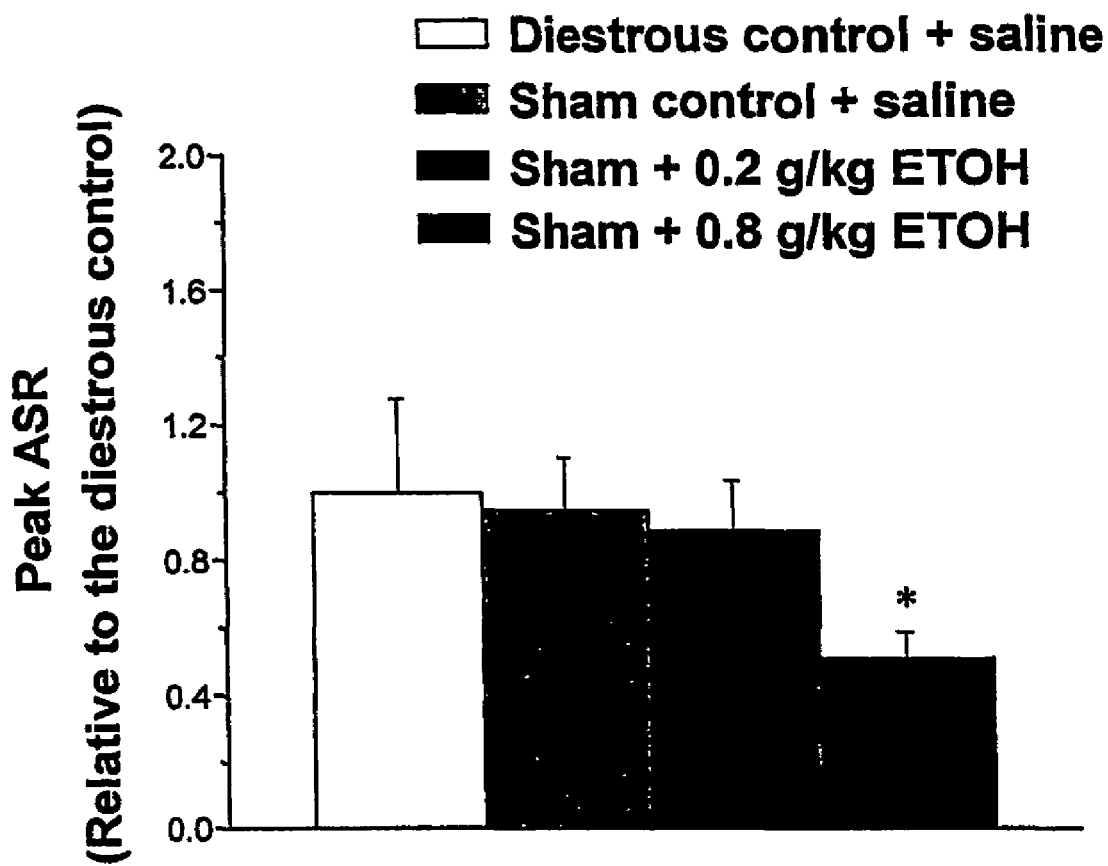

Effects of 4,5,6,7-tetrahydroisoxazolo[5,4-c]pyridin-3-ol on the Acoustic Startle Response In the next step the effects of a GABA partial agonist, 4,5,6,7-tetrahydroisoxazolo[5,4-c]pyridin-3-ol was tested, which has greater potency at $\alpha 4\beta\delta$ subunit isoforms of the $GABA_A$ receptor than at the predominant native $GABA_A$ receptor isoforms expressed in CA1 hippocampus (6). In this case, either 4,5,6,7-tetrahydroisoxazolo[5,4-c]pyridin-3-ol or vehicle was administered 30 minutes before ASR testing. A 3 mg/kg i.p. dose of 4,5,6,7-tetrahydroisoxazolo[5,4-c]pyridin-3-ol significantly (P<0.05) attenuated the ASR by 70% in P withdrawn animals, but exerted the opposite effect in control animals, increasing the ASR by about 40% (P<0.05, FIG. 2). These results are consistent with the observation that $\alpha 4\beta\delta$ subunit isoforms of the $GABA_A$ receptor are increased after P withdrawal, and suggest that activation of this receptor subunit combination produces an effect similar to low dose ethanol.

Methods

Elevated Plus Maze

This device consists of four 10×50 cm arms at 90° angles, with two arms enclosed by 40 cm walls, and two open arms, all elevated 50 cm above the floor. The open arms are also partially bordered by small rails extending to the proximal half of the arm, and the floor of the maze is marked with grid lines every 25 cm. After a 30-45 minutes acclimation period, each animal was placed in the center of the maze 10 minutes after ethanol administration, and exploratory activity recorded for 10 minutes. In some cases, animals were tested 10 minutes following rapid insertion and removal of a needle coated with DMSO, i.p., to replicate the aversive qualities of an ethanol injection. Both number of entries and duration of time spent in the open and closed arms were tabulated, as were the total arm entries, a measure of general activity level. To be considered an open arm entry, the animal had to cross the line of the open platform with all four paws. An increase in open arm entries or time spent in the open arm versus the total time is considered to be a measure of decreased anxiety, (25).

Average values for ethanol-induced changes in peak GABA-gated current and the ASR were evaluated across drug-treatment groups by one-way analysis of variance (ANOVA) with a post-hoc Tukey's test. Data from the plus maze were analyzed in an ANOVA followed by post hoc t-tests (Fisher's PLSD). A P value <0.05 was used as an indication of statistical significance.

Results

Effects of Ethanol on the Elevated Plus Maze

Figure 3:
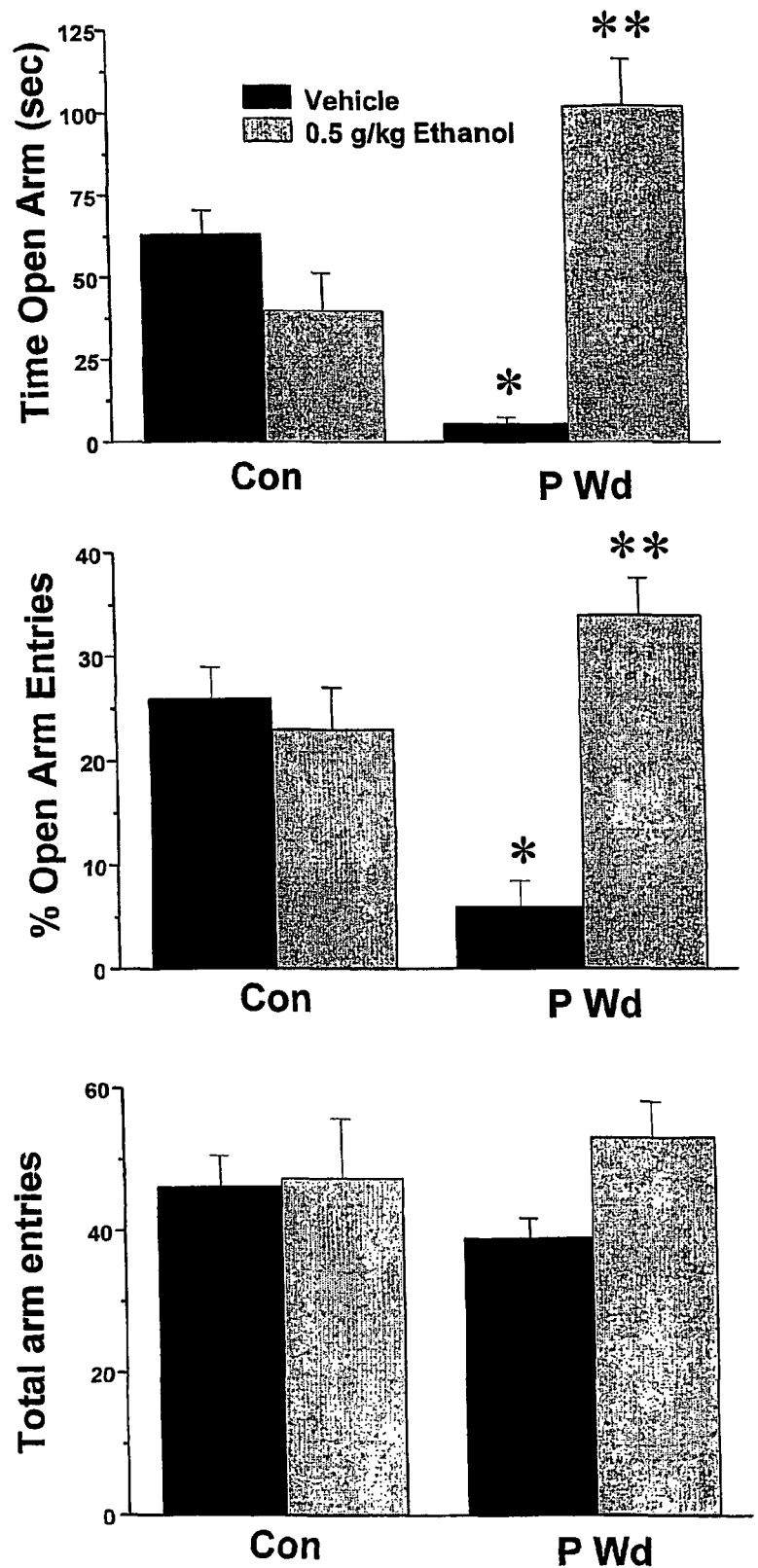
FIG. 3 graphically illustrates the effect on the elevated plus maze after progesterone withdrawal.

It was observed that a low dose (0.5 g/kg) of ethanol significantly (P<0.05) increased the time in the open aim more than 20-fold and also increased the % of open arm entries by 7-fold compared to vehicle in P withdrawn animals (FIG. 3) (These values are 3-fold and 50% greater than those observed for control animals, respectively, after ethanol administration.) In contrast, this dose of the drug produced no significant effect on these parameters tested in control animals. Locomotor activity was unaffected by this dose of ethanol in the study, as assessed by the total number of arm entries, which was not significantly altered in either group of animals tested (FIG. 3). Therefore, these results suggest that, consistent with the results from the ASR study, a low dose of ethanol, which is ineffective in reducing anxiety in control animals, has significant anxiolytic effects after P withdrawal.

An additional study was conducted to test for the possibility that the stress produced by an ethanol injection was different in control and P withdrawal animals. To this end, a separate group of animals was tested on the elevated plus maze following rapid insertion of a DMSO-coated needle to simulate the irritation produced by ethanol injection. There was no significant change in open arm entries in either group, where this stimulus decreased open arm entries by 10±4% for the control group, and by 8±3.6% for the progesterone withdrawal group. Closed arm entries were decreased by 31±11.5% for the controls, but increased 30±14% for the P withdrawal group, a change which was not significant. In addition, the stimulus produced no significant change in locomotor activity, increasing total arm entries by 18±9% (control group) and 28±12% (P withdrawal).

Example II

Materials and Methods

Materials

Adult, female Long Evans rats (140-180 g), housed in groups of three, were employed for all experiments. Animals were maintained under constant conditions of the light/dark cycle (14:10) and temperature (21° C.), with free access to food and water. In all cases, animals were sacrificed at 11:00-13:00 hour of the light cycle. Control animals were tested on the day of diestrus, a low hormone state. All procedures were carried out with the approval of the Institutional Animal Care and Use Committee.

Methods

Steroid and Ethanol Administration Procedures

Animals were administered steroids using one of two protocols: (i) For the 48 hour steroid administration protocol, animals were injected with 10 mg/kg 3α, 5β THP in oil, i.p., on a daily basis for three days and sacrificed 1-2 hour following the final injection. Controls were injected with oil vehicle. (ii) For the progesterone withdrawal paradigm, animals were implanted subcutaneously in the lower back with a silicone capsule (Nalgene Co.1=16 00 1=8 00 o.d., 10 mm/100 g body weight) filled with crystalline progesterone for 21 days, as previously described (51). At this time, the capsule was removed and the animals were injected with 17 β estradiol (2 µgs/animal) in order to reset their cycle. Animals were sacrificed 24 hours later. In the absence of progesterone withdrawal, this estradiol injection paradigm did not result in alterations in α4 expression. In all cases, implantation and removal of capsules were performed under halothane anesthesia. Both paradigms result in brain levels of steroids, which are in the physiological range (51). Although differences in potency and efficacy for the 5α and 5β isomers of THP have been reported (3), our results indicate that with in vivo administration across a 48 hour period, both isomers produce similar effects on GABAR physiology, kinetics and a subunit upregulation (23, 30). Therefore, this study employed the 5β isomer of the steroid.

In some groups of animals, either ethanol (0.5 g/kg in saline) or saline vehicle was administered i.p. (3×, every 40 minutes) for the final 2 hours of the respective steroid administration or withdrawal paradigm. The use of multiple injections of low doses of ethanol would approximate ethanol consumption in the human more closely than would a single injection. For the 48 hour steroid administration paradigm, animals received their first ethanol injection immediately after the steroid injection, and subsequent injections at 40 minute intervals. In all cases, animals were sacrificed 40 minutes after the final ethanol injection (2 hours after the first ethanol injection and final steroid injection). All animal protocols were carried out with the approval of the Institutional Animal Care and Use Committee.

Statistical Analysis

Average values for the optical density of the $\alpha$ band were standardized to the GAPDH control and compared between steroid and steroid/ethanol treatment groups versus control. Average values for LZM potentiation of peak GABA-gated current across the concentration range were compared between steroid/ethanol treatment groups versus control. In both cases, the statistical significance of the data was evaluated across drug-treatment groups using a one-way analysis of variance (ANOVA) with a post-hoc Tukey's test for unequal replications. A P value <0.05 was used as an indication of statistical significance.

Western Blot Protocol

Hippocampi removed from steroid or vehicle-treated animals were homogenized, and membranes prepared as previously described (65). Following electrophoresis on 8% SDS polyacrylamide gels, membranes were transferred to a nitrocellulose membrane (Bio-Rad, Hercules, Calif.). $\alpha 4$ subunit levels were detected by evaluating the band density at 67 kDa after probing with a polyclonal antibody (64). Membranes were incubated for 1-2 hours at room temperature with a 1:5000 dilution of horseradish peroxidase-conjugated donkey anti-rabbit IgG (Amersham, Arlington Heights, Ill.), and visualized with enhanced chemiluminescence with varying concentrations of protein in the linear range. Immunoreactive band densities were quantified using a CCD camera (UMAX Scanner) and one-Dscan software, which uses multiple Gaussian fits to achieve accurate band density profiles. Results were standardized to a glyceraldehyde-3-phosphate dehydrogenase (GAPDH control protein (36 kDa band).

Electrophysiology Protocol

Whole cell patch clamp recordings were carried out on pyramidal neurons acutely dissociated from CA1 hippocampus, as described (65).

Initially, tissue was digested at 32° C. for 50-60 minutes under 100% O2 in PIPES-buffered saline containing (in mM): NaCl 120, KCl 5, CaCl2 1, MgCl2 1, d glucose 25, PIPES 20 and trypsin (type XI, sigma), 0.8 mg/ml, pH 7.0. Following a 1 hour enzyme-free incubation at room temperature, tissue was dissociated by trituration in 1 ml of 20 mM HEPES-buffered DMEM which was replaced by recording medium following transfer to the recording chamber. GABA-gated current was recorded at room temperature (20-25° C.) at a holding potential of −50 mV in a bath containing (in mM): NaCl 120, CsCl 5, CaCl2 2, MgCl2 1, TEA Cl 15, 4-aminopyridine 5, HEPES 10 and glucose 25, pH 7.4, 320 mOsm/kg $H_2O$. The pipette solution contained (in mM): N-methyl-d glucamine chloride 120, Cs4 BAPTA 5 and Mg-ATP 5. The ATP regeneration system tris phosphocreatine (20 mM) and creatine kinase were added to minimize GABA rundown. All drugs were obtained from Sigma Chemical Co, (St. Louis, Mo.), or Calbiochem (BAPTA).

In order to determine functional expression of a containing GABAR, BDZ modulation of GABA ($EC_{20}$)-gated current was determined across steroid and ethanol administration groups. GABA-gated current recorded from $\alpha\chi\beta\gamma2$ GABAR is significantly potentiated BDZs, when x=1-3, 5 (75). However, GABARs containing $\alpha 4$ or $\alpha 6$ are relatively insensitive to BDZ modulation (75, 80). Therefore, potentiation of GABA-gated current by increasing concentrations of the BDZ lorazepam (LZM, 0.1-10 μM) was assessed in order to pharmacologically characterize the GABAR expressed following the treatment paradigms. Deliver of LZM to the isolated neuron was accomplished with a gravity-feed, solenoid controlled, superfusion system positioned within 50-100 μM of the cell, which yielded approximate 40-100 ms exposure times. Peak current was calculated for all drug concentrations as percentage GABA potentiation relative to the current gated b 10 1 GABA. Currents were recorded using an Axopatch 1D amplifier (Axon Instruments) filtered at 2 kHz (four-pole Bessel filter) and detected at 500 Hz (pClamp 5.1). Decay time constants for macroscopic currents were approximated as monoexponential functions using non-linear curve fitting routines with Levenburg-Marquardt algorithms (Origin software, Microcal).

Results

Two-hour Ethanol Exposure and a Subunit Regulation

Figure 4:
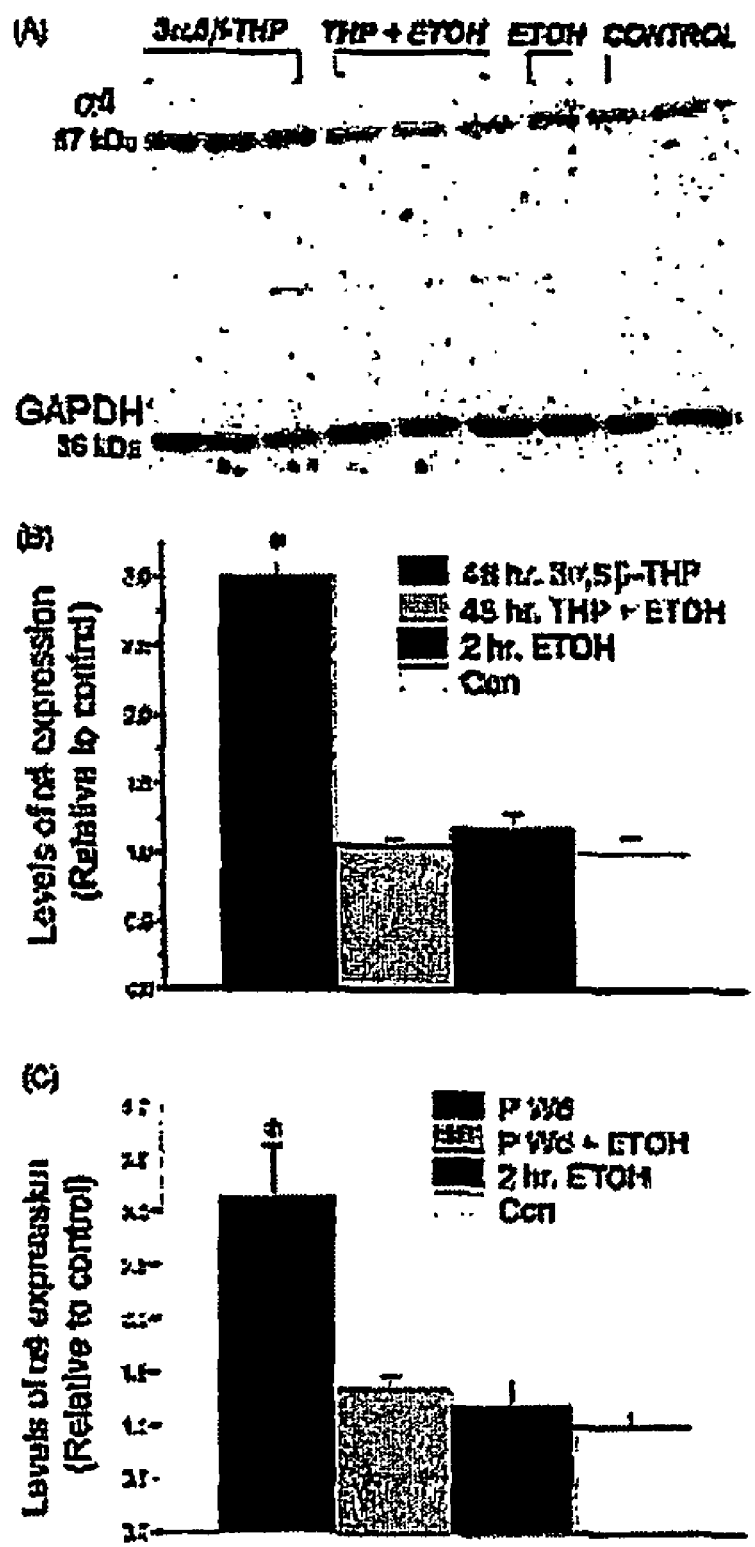
FIG. 4A is a representative western blot of GADPH expression following the administration of ethanol across the final 2 hours of 3$\alpha$,5$\beta$-THP administration.
FIGS. 4B-4C graphically depict the same.

Because ethanol is known to regulate expression of the GABAR $\alpha 4$ subunit (14, 44) tests were run to determine whether acute ethanol administration would alter $\alpha$ expression during a 11-48 h $3\alpha$, $5\beta$-THP administration paradigm known to increase $\alpha 4$ expression (23). Intraperitoneal administration of 0.5 g/kg ethanol across the final 2 hours of $3\alpha$, $5\beta$-THP administration in fact reversed the increase in a expression normally seen at this time in hippocampus (FIGS. 4A,B). This ethanol-steroid paradigm resulted in levels of $\alpha 4$ expression not significantly different from control. In contrast, as previously shown, 48 hours of exposure to $3\alpha$, $5\beta$-THP increased a expression threefold compared to control (FIGS. 4A, B), following saline administration. When administered without steroid, however, ethanol produced no significant effect on $\alpha$ levels (FIGS. 4A, B).

Similar effects were seen after withdrawal from $3\alpha$, $5\beta$-THP following chronic treatment with the parent compound progesterone. The robust threefold increases in $\alpha 4$ expression produced by steroid withdrawal were also reversed by the 2 hour ethanol administration protocol, when levels of $\alpha 4$ expression were unchanged from control levels (FIG. 4C).

Alterations in $\alpha 4$ Expression and Benzodiazepine Sensitivity

Because GABARs containing the a subunit exhibit $\alpha 4$ unique pharmacological profile characterized by an insensitivity to modulation by classic BDZ agonists (75, 80), the responsiveness of acutely isolated CA1 hippocampal pyramidal cells to modulation by the BDZ LZM following 48 hour steroid exposure with or without 2 hour ethanol administration was tested. The ethanol-induced decrease in $\alpha 4$ expression restored the GABA-modulatory effects of LZM following 48 h $3\alpha$, $5\beta$-THP treatment. Under these conditions, LZM potentiated GABA-gated current in a concentration-dependent manner, with a maximal 90% potentiation by 10 1 LZM (FIGS. 5A,B).

In contrast, in saline-treated rats, the increased hippocampal expression of the $\alpha 4$ subunit produced by 48 hours of $3\alpha$, $5\beta$-THP exposure was associated with a relative BDZ insensitivity. In this case, only the highest 10 μM concentration produced minimal (12-15%) potentiation of GABA-gated current, as expected for increased expression of BDZ-insensitive α4 containing GABARs.

Figure 5:
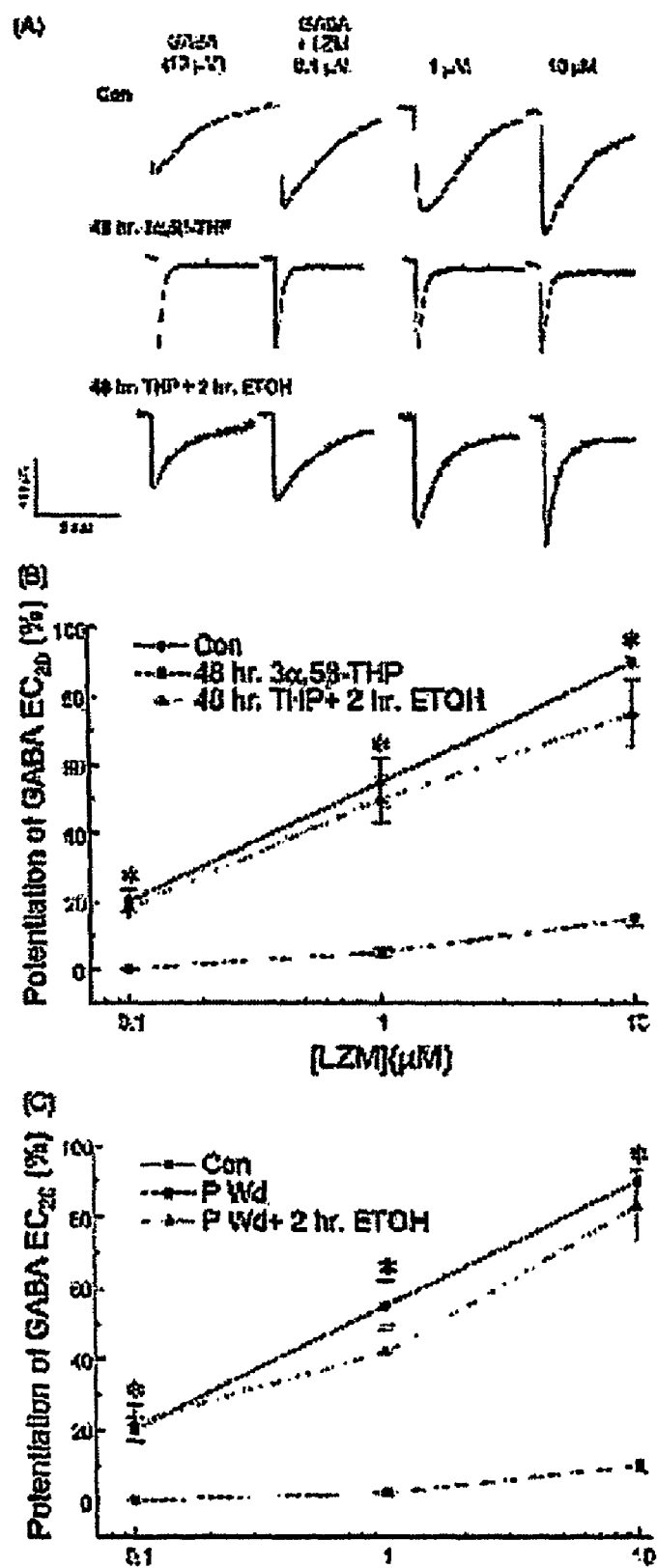
FIGS. 5A-5C graphically depict the responsiveness of acutely isolated CA1 hippocampal pyramidal cells to modulation by the BD2 L2M following 48-hour steroid exposure with or without 2 hours of ethanol administration.
Figure 6:
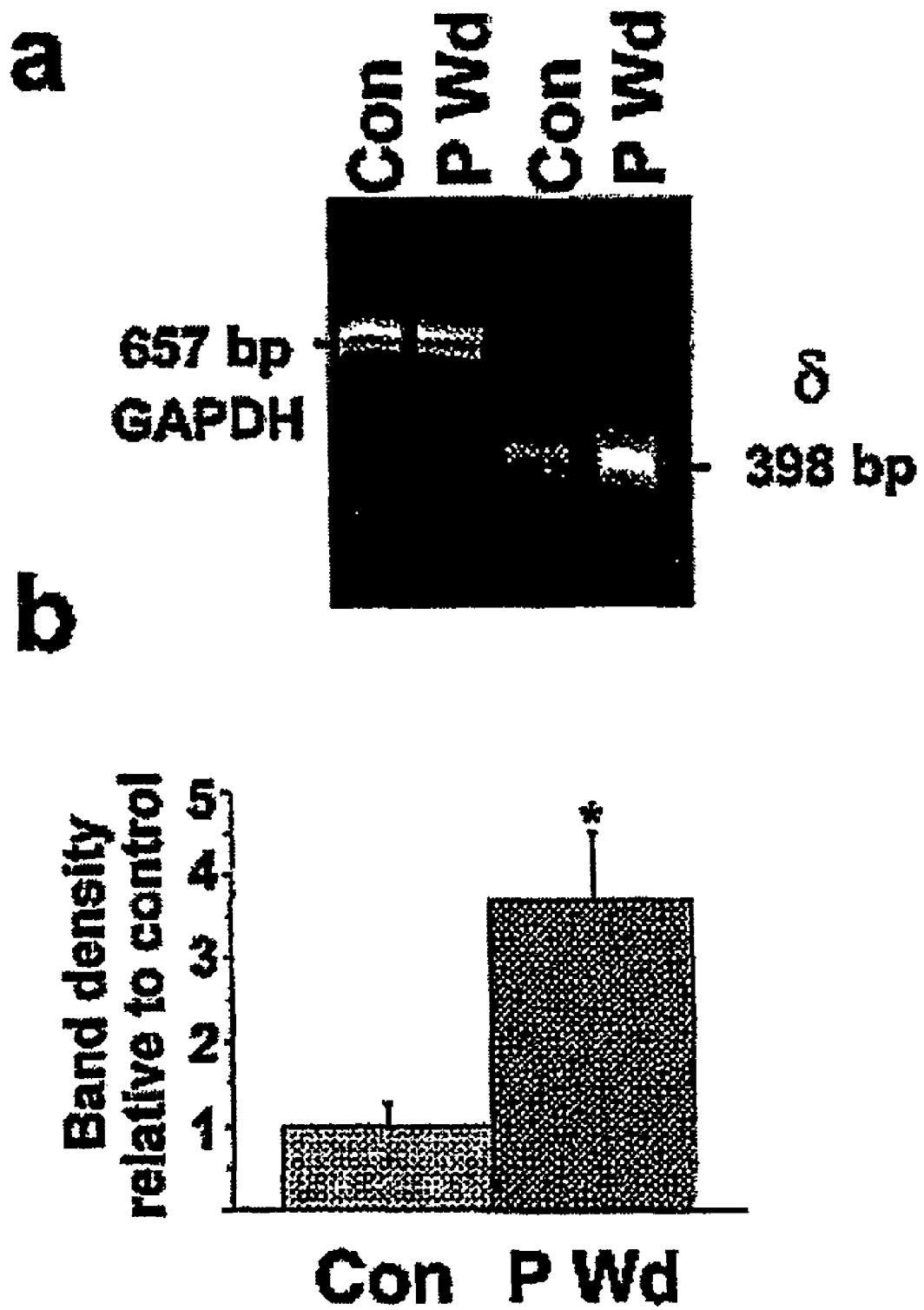
FIG. 6A is a representative northern gel showing the effect of progesterone withdrawal (PWd) on levels of GADPH mRNA as compared to controls (CON)
FIG. 6B graphically depicts the same.
Figure 7:
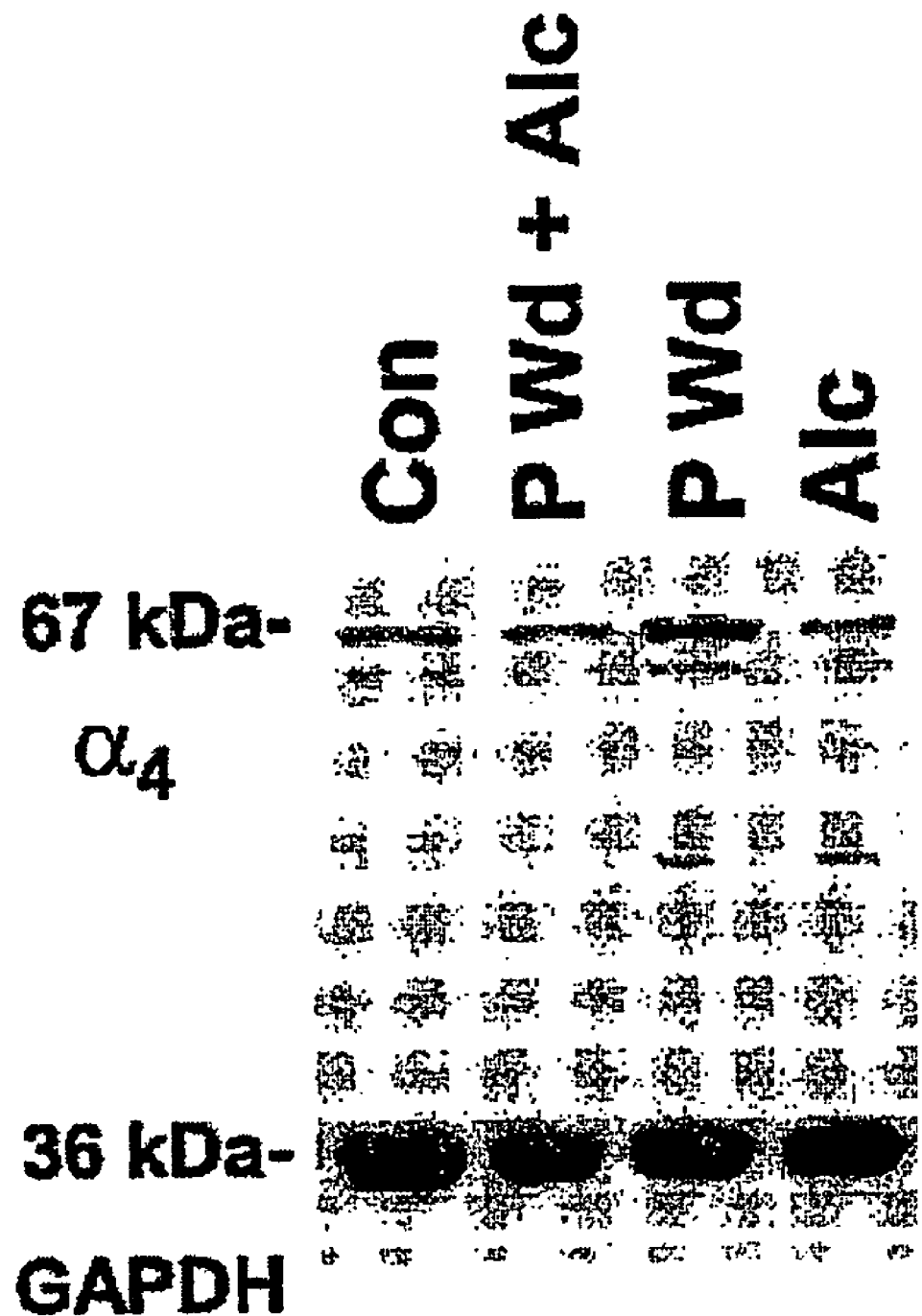
FIG. 7 is a representative western blot of the $\alpha_4$ GABA$_A$ receptor subunit in rat hippocampus after progesterone withdrawal (PWd).
Figure 8A:
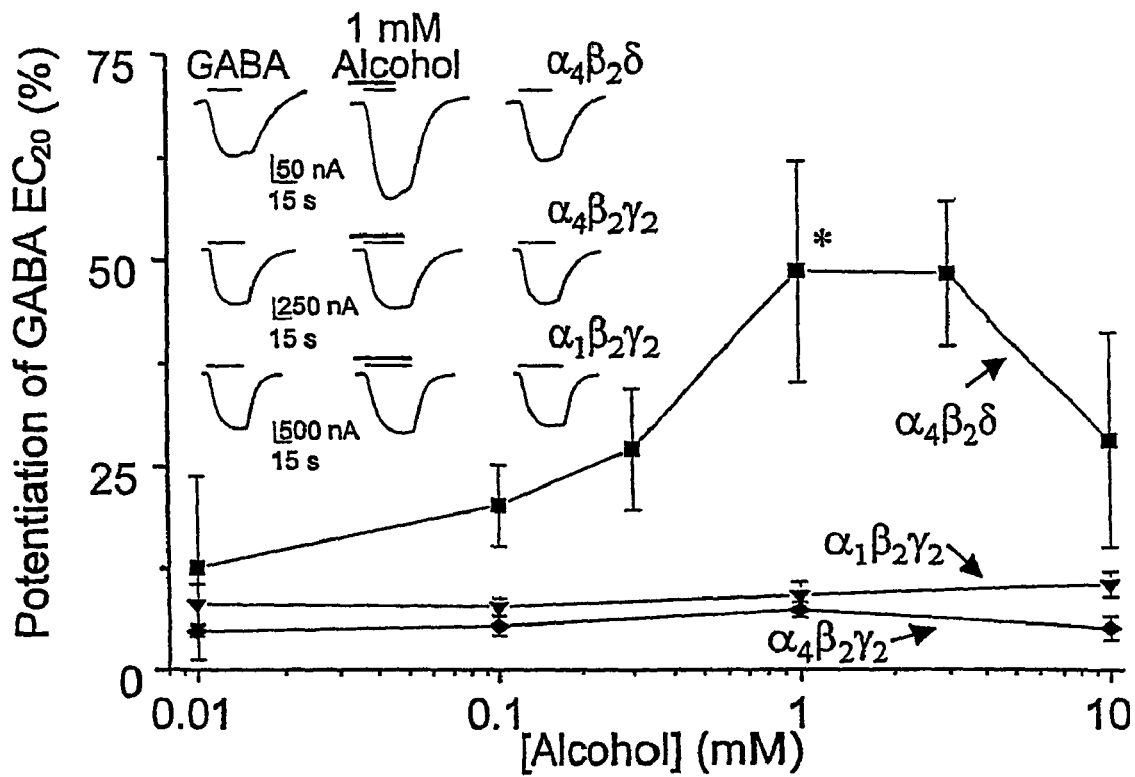
FIGS. 8A-8B graphically illustrate the effect of low concentrations of alcohol on different subtypes of recombinant GABA$_A$ receptors expressed in *Xenopus laevis* oocytes.
Figure 8B:
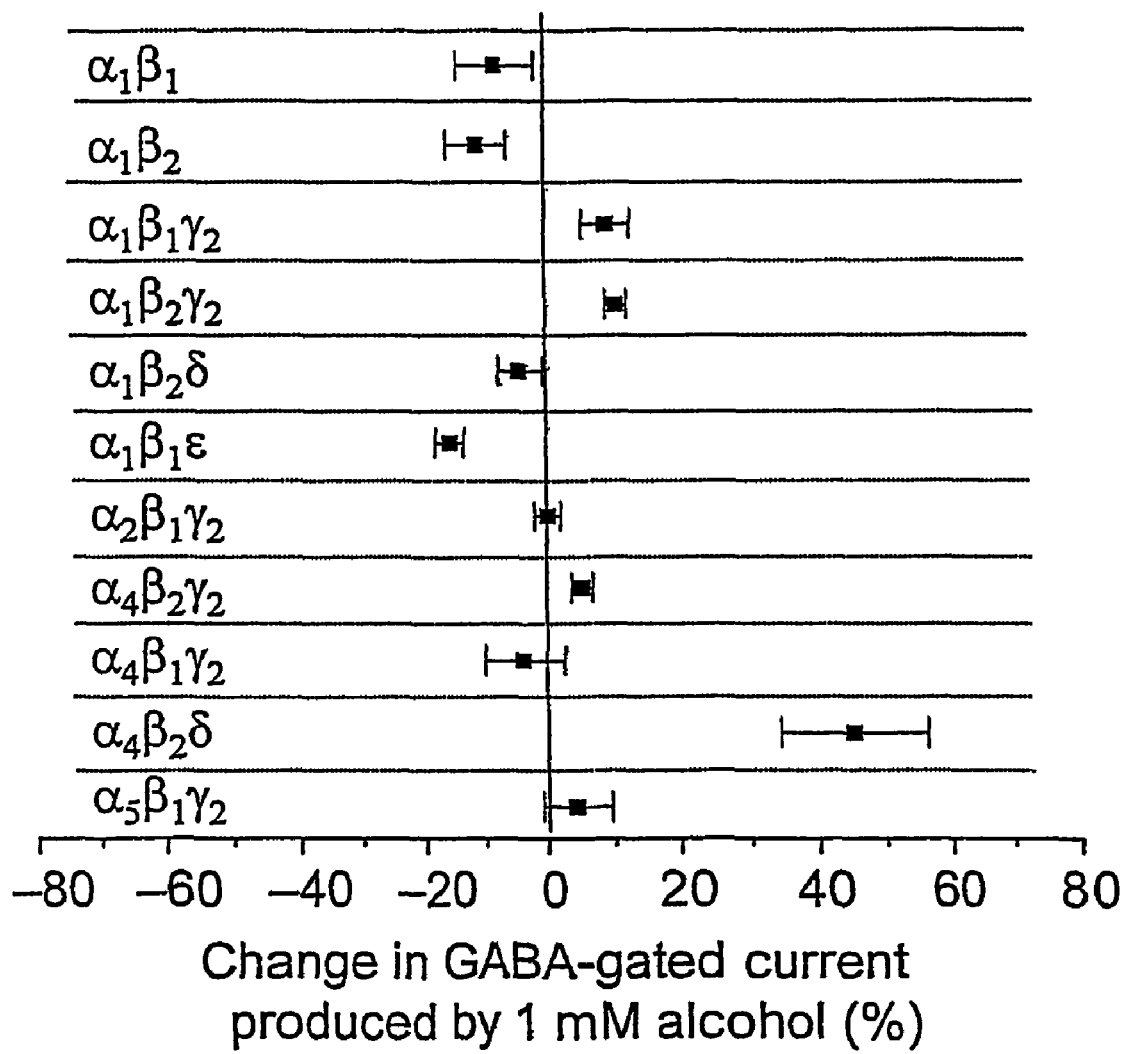

In addition to restoring BDZ potentiation of GABA-gated current, sustained exposure to low dose ethanol during the final 2 hours of the 48 h 3α, 5β-THP administration also resulted in current with a decay time significantly slower (P<0:001) than observed following steroid administration (FIG. 5A, s ⅓43:12 0:4 s, THP p ETOH;s ⅓40:60 0:054 s, THP;s ⅓43:25 0:5 s, control). In contrast, 48 hours of 3α, 5β-THP administration produced an acceleration in decay compared to control (P<0:05). The decrease in α4 expression produced by 2 hours of ethanol administration following progesterone withdrawal also resulted in robust LZM-induced potentiation of GABA-gated current (FIG. 5C) in contrast to the BDZ-insensitive state normally associated with the steroid withdrawal paradigm (64).

Example III

Materials and Methods

Expression of Recombinant $GABA_A$ Receptors and Recording in Oocytes

Plasmids with inserts encoding $GABA_A$ receptor subunit sequence for rat $α_1$ (62), rat $β_2$ (83), rat $α_2$ (62), rat $α_5$ (62), mouse $α_4$ (37), mouse $β_3$ (82), rat $β_1$ (83), rat $γ_{2S}$ (63), human δ (12), and human ε (11) were produced by subcloning each separately into an appropriate cloning vehicle such as PCDM8, pCDNA3.1 or pGHEMHE vectors (Invitrogen, Carlsbad Calif.) using a T7 promoter and standard subcloning techniques (59). Plasmids were linearized with an appropriate restriction enzyme at a site 3' to the insert and cRNAs were synthesized using T3 or T7 polymerase (mMessage mMachine, Ambion, Tex.). The size of the cRNA was verified and RNA was quantified by ethidium bromide staining after electrophoresis on 1% agarose gels.

The preparation, injection, and maintenance of oocytes were carried out as described previously (78). Oocytes were injected with receptor subunit cRNAs (2 to 20 ng) in the following ratios: $α_1$:$β_1$:$γ_{2S}$, $α_1$:$β_2$:$γ_{2S}$ and $α_1$:$β_1$:$ε_1$, 1:1:1; $α_2$:$β_1$:$γ_{2S}$, $α_5$:$β_1$:$γ_{2S}$, $α_4$:$β_1$:$γ_{2S}$, and $α_4$:$β_2$:$γ_{2S}$, 10:1:1; $α_4$:$β_1$: δ, $α_4$:$β_2$:δ, $α_4$:$β_3$δ, 10:1:10; $α_1$:$β_2$:δ, 1:1:10 or 1:0.5:3; $α_1$:$β_1$: δ, 1:1:10 or 1:0.5:3; $α_2$:$β_1$:δ and $α_2$:$β_2$:δ, 1:0.5:3; $α_1$:$β_1$, $α_1$:$β_2$, $α_2$:$β_1$, $α_2$:$β_2$, $β_2$:$γ_{2S}$ and $α_4$δ, 1:1, $α_4$:$β_1$, $α_4$:$β_2$, $α_4$:$β_3$, 10:1, $β_2$δ, 1:10.

Voltage-clamp recording was carried out 1 to 3 days after injection of cRNAs. Electrodes were filled with 3 M KCl and had resistances of 0.4-4 MΩ. Oocytes were positioned in a small Perspex chamber and continuously superfused with a saline solution (100 mM NaCl, 2 mM KCl, 1.8 mM $CaCl_2$, 10 mM HEPES, pH 7.5). Agonists and modulators were both applied in the same saline solution. Oocytes were voltage-clamped at −70 mV and macroscopic currents were recorded with a two-electrode voltage-clamp using a Warner Instruments OC-725 amplifier as described previously (79). Currents were recorded on a chart recorder or by using Axograph on a Macintosh computer. Oocytes injected with $β_2$, $α_4β_2$, $β_2γ_{2s}$ or $α_4$δ gave little (1-5 nA) or no response to even high concentrations of GABA. In oocytes injected with $α_4$+$β_2$+δ subunits, the ratio of currents induced by THIP: GABA was 1.24, consistent with an action of THIP at heteromeric $α_4β_2$δ receptors (1,16). In addition, lanthanum ($La^{3+}$, 300 μM inhibited by 80% currents at $α_4β_2$δ receptors, an action specific for this receptor subtype (60).

Other subunits ($α_1$, $α_2$, $β_1$, $β_2$) were tested for co-expression with the δ subunit. Because functional receptors can assemble from some α+β subunits in the absence of a δ subunit, it is necessary to distinguish the properties of αβδ receptors from those of αβ receptors. Although $α_1β_2$δ receptors are inhibited by zinc, they are significantly less sensitive to zinc than are $α_1β_2$ receptors (61). Thus, the differential sensitivity to zinc was used (1 μM) to distinguish oocytes expressing $α_1β_2$δ receptors from those expressing $α_1β_2$δ receptors when injected with $α_1$+$β_2$+δ subunits. For 7 of 22 oocytes injected with $α_1$+$β_2$+δ, zinc inhibition (49.1±6.4%) was significantly less (P<0.0005) than for $α_1β_2$ receptors (72.4±6.9%; n=5), suggesting incorporation of the δ subunit within receptors in these oocytes. For the other 15 oocytes, zinc inhibited GABA currents by a mean 66.4±6.4%, a value not significantly different (P=0.338) from that for $α_1β_2$ receptors. Alcohol did not affect responses to GABA at these receptors, which were 88-95% of control in oocytes injected with $α_1$+$β_2$ or with $α_1$+$β_2$+δ. It was also determined that in the receptors containing the $β_1$ rather than the $β_2$ subunit, all oocytes injected with $α_1$+$β_1$+δ expressed receptors whose sensitivity to zinc was indistinguishable from that of $α_1β_1$ receptors. Again, GABA responses at these receptor subtypes were not altered by 1 mM alcohol. Oocytes injected with combinations of $α_2β_1$δ, $α_2β_2$δ, $α_4β_1$δ and $α_4β_3$δ did show any response to GABA, suggesting lack of expression of functional GABA receptors.

Statistical Analysis

Average values for peak current (THIP, GABA), alcohol-induced changes in peak GABA-gated current and the acoustic startle response were evaluated across drug-treatment groups by one-way analysis of variance (ANOVA) with a post-hoc Tukey's test. A P value <0.05 was used as an indication of statistical significance. (Supported by AA 13646 to N.L.H.)

Progesterone Withdrawal

Crystalline progesterone was administered via a silicone capsule (1/16" i.d., 1/8" o.d.) implanted subcutaneously (10 mm length/100 gm body weight) in female rats (110-120 grams, in vitro studies; 220-250 grams, behavioral studies) for 21 days. Control rats were implanted with an empty capsule. This paradigm has been shown to result in hippocampal levels of 3α, 5α-THP in the physiological range (65). Animals were tested 24 hours after removal of the implant.

Western Blot Analysis

Membranes prepared from hippocampal tissue were solubilized and electrophoresed on 9% SDS-polyacrylamide gels before transfer to a polyvinyldifluoride membrane, as described (65,69). Polyclonal antiserum against the δ subunit ($Asr^{318}$-$Leu^{400}$) was supplied by Dr. R. McKernan (Merck) (56) and is visualized as a 54 kDa band. Membranes were also probed with an antibody for the $α_4$ $GABA_A$ receptor subunit (67 kDa) (64), developed according to a previously described protocol (38), and a commercial antibody for the control protein GAPDH (glyceraldehyde-3-phosphate dehydrogenase; 36 kDa). Membranes were incubated for 1-2 hours at room temperature with 1:10,000 ($α_4$), 1:7,000 (δ) or 1:20,000 (GAPDH) dilution of antibody followed by addition of 1:5,000 horseradish-peroxidase-conjugated donkey anti-rabbit IgG (Amersham). Band densities were quantified using densitometry with One-Dscan software after normalization to the GAPDH control. Reagents were obtained from Sigma/Genosys.

Co-Immunoprecipitation

Receptors were initially solubilized from hippocampal membranes using 0.5% Na deoxycholate and centrifugation at 120,000 rpm, as described (68,46). The solubilized receptor preparation (0.8 mg) was incubated overnight with 10 μl anti-δ (56) or a negative control antibody (anti-β-NAC, a cytosolic protein (77) bound to Protein A beads (68). This mixture was then washed three times with TBS/0.05% TWEEN-20/0.05% NP40 before eluting with 0.1 M glycine/ HCl, pH 2.5, followed by low speed centrifugation. Proteins in the supernatant were precipitated with 10% trichloroacetic acid, washed with acetone and resuspended in sample buffer. Immunoprecipitated proteins in the final suspension were separated using gel electrophoresis (8% SDS-PAGE gel with an acrylamide:bis ratio of 30:1.2) and probed with a digoxygenin-labeled $\alpha_4$ antibody (39) (Roche Molecular Biochemicals) at a 1:400 dilution of the original serum. Initially, the $\alpha_4$ antibody (1 ml) was purified on a Sephadex G-25 column using Hepes-KOH, pH 8.3, and then labeled with digoxygenin (1.5 mg digoxygenin/1.9 mls α4 eluate) for 1.5 hours at room temperature, followed by re-purification on the Sephadex G-25 column using PBS/20 mM Tris. Anti-digoxygenin conjugated to horseradish peroxidase (poly, F(ab)$^2$ fragments, Roche Molecular Biochemicals 1:45,000) was used as a secondary antibody, with 1.5% milk as the blocking agent. Following a 1 hour incubation, the resulting band for the digoxygenin-labeled $\alpha_4$ antibody was visualized with ECL chemiluminescence (ECL Plus, Amersham Pharmacia Biotech). Optical density could not be quantified because $\alpha_4$ levels were barely detectable under control conditions; therefore, it was virtually an all-or-none response.

Semi-Quantitative RT-PCR

Following isolation of total RNA from hippocampus, reverse transcription (SuperScript II, Rnase RT, GibcoBRL) yielded complementary DNA (cDNA) which was amplified with PCR methods (65) using oligonucleotide primers for the δ subunit (398 bp)(70) and GAPDH (657 bp, Operon). Twenty three to thirty amplification cycles were used for two different concentrations of cDNA (25 or 50 ng) to detect band densities within a linear range (15). Following gel electrophoresis (FMC Bioproducts), the density of DNA bands stained with ethidium bromide was quantified and normalized to the GAPDH control.

Whole Cell Patch Clamp Electrophysiology

Following progesterone withdrawal or control conditions, pyramidal cells were acutely isolated from CA1 hippocampus as described (65,64). GABA-gated Cl$^-$ currents were recorded using whole cell patch clamp techniques at a holding potential of −50 mV. An ATP-regeneration system was included in the pipet to prevent run-down of GABA-gated currents, and drugs were applied using a pipet array that yielded 40-100 msec exposure times.

Acoustic Startle Response

Animals were tested in a stabilimeter device (SR-Lab Startle Response System, San Diego Instruments, Inc.) that permitted vertical movement of a Plexiglas cage contained within a lit, well-ventilated, sound-attenuating chamber. The amplitude of movement was detected by a piezoelectric device with a voltage output proportional to cage displacement. The analog output of the accelerometer was amplified and digitized before computer analysis (15). Five minutes following intraperitoneal administration of alcohol (0.2 or 0.4 g/kg) or saline vehicle (1.5 ml volume), animals were placed in the chamber for 5 a minute acclimation period. Five acoustic stimuli (116 dB, 40 msec duration) were then presented once every 10-15 seconds via a white-noise generator through speakers positioned on either side of the cage. For each acoustic stimulus, the integrated response (amplitude and duration) was averaged across a 100 msec post-stimulus time period and the response latency determined. Both values were normalized to the weight of the animal. Values for the integrated response for the first noise stimulus following administration of each dose of alcohol were averaged and expressed as a fraction of the saline control average for the indicated treatment (P Wd versus control) group. This paradigm has been used to demonstrate the anxiolytic effects of low doses of alcohol in alcohol-preferring rats (34), a model of increased alcohol consumption. It is routinely used to assess behavioral excitability following withdrawal from benzodiazepiness (48) and alcohol (73), and is known to be modified by GABA modulators, such as diazepam (11), and by local infusion of excitatory compounds into dorsal hippocampus (85).

Results

The $\alpha_4\beta\delta$ GABA$_A$ receptors are expressed at very low levels in most regions of the brain (55). Predicting that physiological states that are associated with increased sensitivity to alcohol (such as PMS) may involve increased expression of $\alpha_4\beta\delta$, the rodent model of PMS 1 was used to test this hypothesis. With chronic in vivo administration and withdrawal of progesterone, the hormonal and behavioral facets of PMS 2 were replicated. Expression of δ and $\alpha_4$ subunit proteins in the hippocampus was three-fold higher after progesterone withdrawal (FIGS. 9a and b), as was δsubunit mRNA. Co-assembly of these subunits was determined using co-immunoprecipitation (FIG. 9c) and verified by an increased efficacy of THIP, a GABA partial agonist, relative to GABA after progesterone withdrawal (FIG. 9d). This is characteristic of $\alpha_4\beta\delta$ receptor expression (1). Co-assembly of $\beta_2$ with $\alpha_4\delta$ has not been tested directly but is suggested by reports of high levels of $\beta_2$ in areas rich in $\alpha_4$ and δ subunits.

Figure 10A:
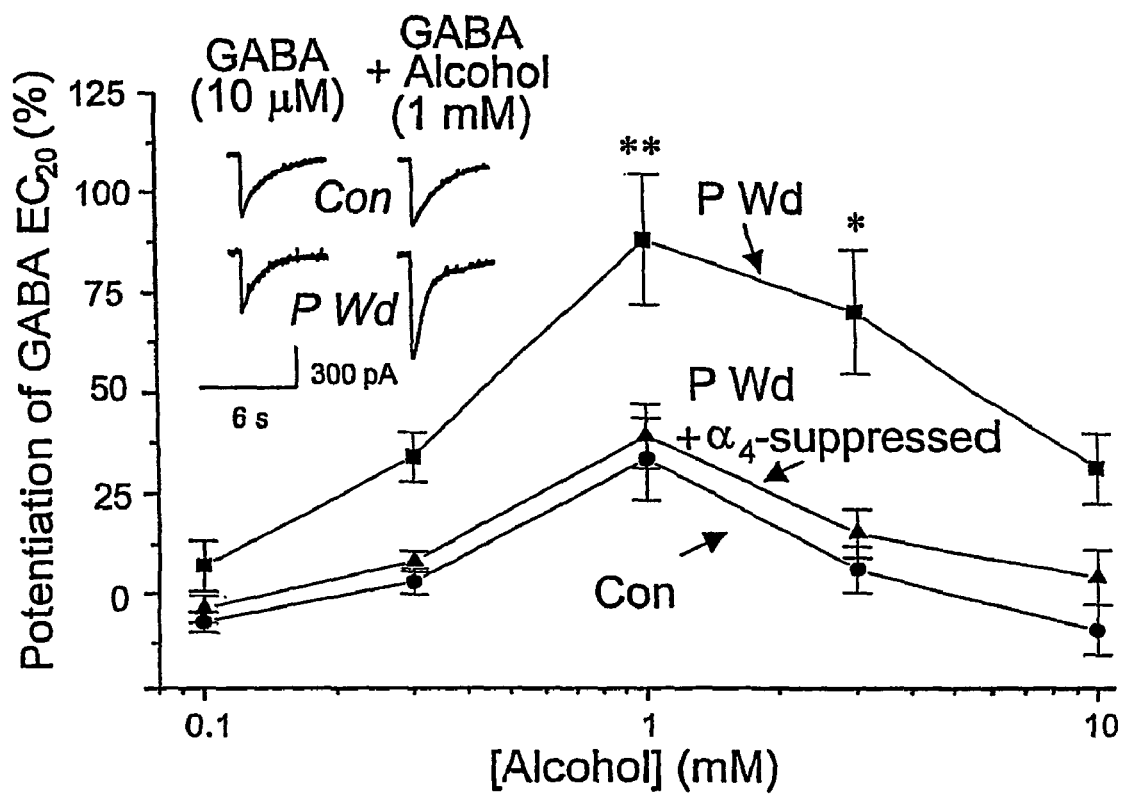
FIGS. 10A-10B graphically depict the effect of low doses of alcohol on GABA-gated currents in hippocampal pyramidal neurons after progesterone withdrawal.
Figure 10B:
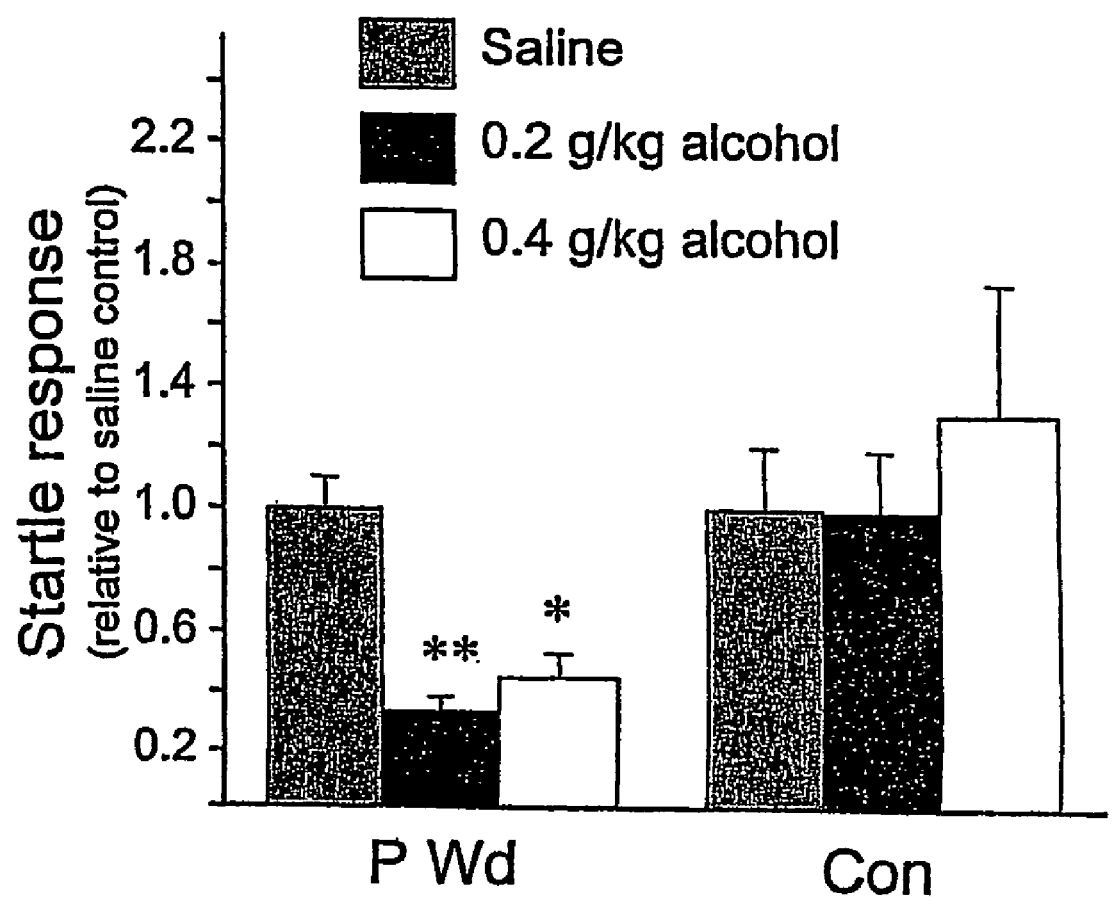

Concomitant with upregulation of $\alpha_4\beta\delta$ receptors in the progesterone-withdrawal model, 1 mM alcohol produced a 81±21% potentiation of GABA-gated currents recorded from hippocampal neurons in vitro (FIG. 10a). Higher concentrations (10 mM and greater) of alcohol were not as effective in potentiating GABA-gated currents. After progesterone withdrawal, low does of alcohol (0.2-0.4 g/kg) administered in vivo also decreased the acoustic startle response, a measure of behavioral excitability, suggesting a greater anxiolytic effect of alcohol at this time (FIG. 10b).

To verify that native $\alpha_4\beta\delta$ receptors were sensitive to low doses of alcohol, the progesterone withdrawal experiments were repeated after suppressing $\alpha_4$ subunit expression. As previously shown that, following progesterone withdrawal, injection of a GABA modulator prevents expression of the $\alpha_4$ subunit (64). Thus, alcohol was used here to suppress expression of the $\alpha_4$ protein following progesterone withdrawal (P Wd+Alc; FIG. 9b). Under these conditions, the GABA-modulatory effects of 1 mM alcohol were prevented in hippocampal neurons (FIG. 10a; P Wd+$\alpha_4$ suppressed), again implicating $\alpha_4\beta\delta$ receptors as sensitive to low doses of alcohol. There is also corroborating evidence that the reinforcing and anti-convulsant properties of alcohol are reduced in transgenic mice lacking the δ subunit (49).

It is thought that $\alpha_4\beta\delta$ receptors are expressed at extrasynaptic sites (55) where they may dampen neuronal excitability, primarily by acting as a resistive shunt (5). Enhanced function of these receptors by low concentrations of alcohol in women with PMS would further decrease neuronal excitability, leading to behavioral stress-reduction. Blood alcohol levels of 1-3 mM may result from consumption of a half glass of wine (35) or less (28). The reported increase in alcohol consumption and propensity for alcoholism in women with PMS (47) may thus be accounted for by these enhanced reinforcing properties of alcohol. More broadly, it is conceivable that alterations in GABA$_A$ receptors, perhaps including α$_4$β$_2$δ, are involved in the genetic predisposition for alcoholism in which there is an increased sensitivity to low doses of alcohol (9).

REFERENCES

1. Adkins, C. E. et al. 2001 *J. Biol. Chem.* 276: 38934-38939.
2. Arnot, M. I., Davies, M., Martin, I. L., and A. N. Bateson. 2001. GABA(A) receptor gene expression in rat cortex: differential effects of two chronic diazepam treatment regimens. *J. Neurosci. Res.* 64: 617-625.
3. Belelli, D., Lambert, J. J., Peters, J. A., Gee, K. W., and N. C. Lan. 1996. Modulation of human recombinant GABA-A receptors by pregnanediols. *Neuropharmacology* 35:1223-1231.
4. Bitran, D., Dugan, M., Renda, P., Ellis, R., and M. Foley. 1999. Anxiolytic effects of the neuroactive steroid pregnanolone (3alpha-OH-5beta-pregnan-20-one) after microinjection in the dorsal hippocampus and lateral septum. *Brain Res.* 850: 217-224.
5. Brickely, S. G., Revilla, V., Cull-Candy, S. G., Wisden, W., and M. Farrant. 2001. *Nature* 409: 88-92.
6. Brown, N., Kerby, J., Bonnert, T. P., Whiting, P. J., and K. A. Wafford. 2002. Pharmacological characterization of a novel cell line expressing human alpha(4)beta(3)delta GABA(A) receptors. *Br J Pharmacol* 136: 965-974.
7. Cagetti, E., Liang, J., Spigelman, I., and R. W. Olsen. 2003. Withdrawal from chronic intermittent ethanol treatment changes subunit composition, reduces synaptic function, and decreases behavioral responses to positive allosteric modulators of GABA-A receptors. *Mol Pharmacol* 63: 53-64.
8. Carta, M., Ariwodola, O. J., Weiner, J. L., and C. F. Valenzuela 2003. Alcohol potently inhibits the kainate receptor-dependent excitatory drive of hippocampal interneurons. *Proc Natl Acad Sci* 100, 6813-6818.
9. Cohen, H. L., Porjesz, B. and H. Begleiter. 1993. The effects of ethanol on EEG activity in males at risk for alcoholism. *Electroencephalogr Clin. Neurophysiol.* 86: 368-376.
10. Davies, P. A., Hanna, M. C., Hales, T. G. and E. F. Kirkness. 1997. Insensitivity to Anaesthetic Agents Conferred by a Class of GABA(A) receptor subunit. *Nature.* 385: 820-823.
11. Davis, M. and D. W. Gallagher. 1988. *Eur. J. Pharmacol.* 150: 23-33.
12. Day, T. M., Hartnett, C., Blankenbiller, K. and T. V. Ramabhadran. Direct Submission. Submitted 01, Aug. 1997. Molecular Biology, Neurogen Corporation, 3 NE Industrial Road, Branford, Conn. 06405, USA.
13. Devaud, L. L., Purdy, R. H., and A. L. Morrow. 1995. The neurosteroid, 3α OH-5 a pregnan-20-one, protects against bicuculline-induced seizures during ethanol withdrawal in rats. *Alcoholism: Clin. Exp. Res.* 19:350.355.
14. Devaud, L. L., Fritschy, J.-M., Sieghart, W., and A. L. Morrow. 1997. Bidirectional alterations of GABAA receptor subunit peptide levels in rat cortex during chronic ethanol consumption and withdrawal. *J. Neurochem.* 69:126-130.
15. Dow-Edwards, D. L. 1996. *Neurotoxicol. And Teratol.* 18: 289-296.
16. Ebert, B. et al. 1997. *Mol. Pharmacol.* 52:1150-1156.
17. Endicott, J. et al. (1999). Is premenstrual dysphoric disorder a distinct clinical entity? *J. Womens Health Gend. Based Med.* 8: 663-679.
18. Engel, S. R., Purdy, R. H., and K. A. Grant. (2001). Characterization of discriminative stimulus effects of the neuroactive steroid pregnanolone. *J Pharmacol Exp Ther* 297: 489-495.
19. Follesa, P., et al. 2000. Allopregnanolone synthesis in cerebellar granule cells: roles in regulation of GABA(A) receptor expression and function during progesterone treatment and withdrawal. *Mol. Pharmacol.* 57: 1262-1270.
20. Frye, C. A. 1995. The neurosteroid 3alpha,5alpha-THP has antiseizure and possible neuroprotective effects in an animal model of epilepsy. *Brain Res.* 696: 113-120.
21. Frye, C. A., and L. E. Bayon, L. E. 1998. Seizure activity is increased in endocrine states characterized b decline in endogenous levels of the neurosteroid 3 α 5 a THP. *Neuroendocrinology* 68: 272-280.
22. Gallo, M. A., and S. S. Smith. 1993. Progesterone withdrawal decreases latency to and increases duration of electrified prod burial: a possible rat model of PMS anxiety. *Phrmacol. Biochem. Behav.* 46: 897-904.
23. Gulinello, M., Gong, Q. H., Li, X., and S. S. Smith. 2001. Short-term exposure to a neuroactive steroid increases a GABAA receptor subunit levels in association with increased anxiety. *Brain Res.* 910: 55-66.
24. Gulinello, M. and S. S. Smith. 2003. Anxiogenic effects of neurosteroid exposure: sex differences and altered GABA-A receptor pharmacology in adult rats. *J. Pharmacol. Exp. Ther.* 305, 541-548.
25. Gulinello, M., Gong, Q. H. and S. S. Smith (2003a). Progesterone withdrawal increases the anxiolytic actions of gaboxadol: role of α4βδ GABA$_A$ receptors. *Neuroreport* 14: 43-46.
26. Gulinello, M., Orman, R. and S. S. Smith (2003b). Sex differences in anxiety, sensorimotor gating and expression of the α4 subunit of the GABA$_A$ receptor in the amygdala after progesterone withdrawal. *Eur J Neuroscience* 17: 641-648.
27. Harris, R. A., Mihic, S. J., Brozowski, S., Hadingham, K. and P. J. Whiting. (1997). Ethanol, flunitrazepam and pentobarbital modulation of GABA-A receptors expressed in mammalian cells and *xenopus* oocytes. *Alc Clin Exp Res* 21, 444-451.
28. Holford, N. H. 1987. *Clin. Pharmacokinet.* 13: 273-292.
29. Holt, R. A., Bateson, A. N., and I. L. Martin. 1996. Chronic treatment with diazepam or abecarnil differently affects the expression of GABAA receptor subunit mRNAs in the rat cortex. *Neuropharmacology* 35:1457-1463.
30. Hsu, F. C., Waldeck, R., Faber, D. S., and S. S. Smith. 2003. Neurosteroid effects on GABAergic synaptic plasticity in hippocampus. *J. Neurophysiol.* 89:1929-1940.
31. Hsu, F. C., and S. S. Smith. 2003. Progesterone withdrawal reduces paired-pulse inhibition in rat hippocampus: dependence on GABA-A receptor alpha-4 upregulation. *J. Neurophysiol.* 89: 186-198.
32. Hyytia, P., and G. F. Koob. 1995. GABA-A receptor antagonism in the extended amygdala decreases ethanol self-administration in rats. *Eur J Pharmacol* 283:151-159.
33. Institute of Laboratory Animal Resources, Commission on Life Sciences, National Research Council. (1996). *Guide for the Care and Use of Laboratory Animals* (Institute of Laboratory Animal Resources, Commission on Life Sciences, National Research Council, 1996).
34. Jones, A. E. et al. 2000. *Pharmacol. Biochem. Behav.* 67:313-318.
35. Kalant, H., LeBlanc, A. E., Wilson, A. and S. Homatidis. 1975. Can. Med. Assoc. J. 112: 953-958.

36. Kamatchi, G. L. et al. 1995. GABAA receptor beta 1, beta 2, and beta 3 subunits: comparisons in DBA/2J and C57BL/6J mice. Biochim. Biophys. Acta. 1261: 134-142.
37. Kawai, J., et al. 2001. Functional annotation of a full-length mouse cDNA collection. *Nature.* 409: 685-690.
38. Kern, W. and W. Sieghart. 1994. *Neurochem.* 62, 764-769.
39. Klausberger, T. et al. 2001. *J. Biol. Chem.* 276:16024-16032.
40. Koob, G. F., Mendelson, W. B., Schafer, J., Wall, T. L., Britton, K. T., and F. E. Bloom (1988). Picrotoxinin receptor ligand blocks anti-punishment effects of alcohol. *Alcohol* 5: 437-443.
41. Lancel, M., Faulhaber, J., Schifelholz, T., Romeo, E., Di Michele, F., Holsboer, F., and R. Rupprecht. (1997). Allopregnanolone affects sleep in a benzodiazepine-like fashion. *J. Pharmacol. Exp. Ther.* 282: 1213-1218.
42. Lau, E. C., Li, Z. Q., Santos, V. and H. Slavkin. 1993. C. *J. Steroid Biochem. Mol. Biol.* 46, 751-758.
43. Lovinger, M., White, G., and F. F. Weight. 1989. Ethanol inhibits NMDA-activated ion current in hippocampal neurons. *Science* 243:1721-1724.
44. Mahmoudi, M., Kang, M. H., Tillakaratne, N., Tobin, A. J., and R. W. Olsen. (1997). Chronic intermittent ethanol treatment in rats increases GABAA receptor a subunit expression possible relevance to alcohol dependence. *J. Neuro. Chem.* 68: 2485-2492.
45. Majewska, M. D., Harrison, N. L., Schwartz, R. D., Barker, J. L., and S. M. Paul. 1986. Steroid hormone metabolites are barbiturate-like modulators of the GABA receptor. *Science* 232:1004-1007.
46. McKernan, R. M. et al. 1991. *Neuron* 7: 667-676.
47. McLeod, D. R., Foster, G. V., Hoehn-Saric, R., Svikis, D. S., and P. A. Hipsley. 1994. Family history of alcoholism in women with generalized anxiety disorder who have premenstrual syndrome: patient reports of premenstrual alcohol consumption and symptoms of anxiety. *Alcohol Clin. Exp. Res.* 18: 664-670.
48. Miczek, K. A. and J. A. Vivian (1993) *Psychopharmacol.* 110: 379-382.
49. Mihalek, R. M. et al. 2001. *Alcohol Clin. Exp. Res.* 25: 1708-1718.
50. Mihic, S. J. et al. 1997. *Nature* 389:385-389.
51. Moran, M., Goldberg, M., and S. Smith. 1998. Progesterone withdrawal II: insensitivity to the sedative effects of a benzodiazepine. *Brain Res.* 807:91-100.
52. Mu, W. Cheng, Q., Yang, J., and D. R Burt. 2002. Alternative Splicing of the GABA(A) Receptor Alpha 4 Subunit Creates a Severely Truncated mRNA. *Brain Res. Bull.* 58:447-484.
53. Peng, Z., Hauer, B., Mihalek, R. M., Homanics, G. E., Sieghart, W., Olsen, R. W., and C. R. Houser. (2002). GABA(A) receptor changes in δ subunit-deficient mice: altered expression of α4 and γ2 subunits in the forebrain. *J Comp Neurol* 446:179-197.
54. Nie, Z., Schweitzer, P., Roberts, A. J., Madamba, S. G., Moore, S. D. and G. R. Siggins. (2004). Ethanol augments GABAergic transmission in the central amygdala via CRF1 receptors. *Science* 303:1512-1514.
55. Nusser, Z., Sieghart, W. and P. J. Somogyi. 1998. *Neurosci.* 18, 1693-1703.
56. Quirk, K., Whiting, P. J., Ragan, C. I. and R. M. McKernan, R. M. 1995. *Eur. J. Pharmacol.* 290: 175-181.
57. Reddy, D., Kim, H., and M. Rogawski. 2001. Neurosteroid withdrawal model of perimenstrual catamenial epilepsy. *Epilepsia* 42:328-336.
58. Roberto, M., Madamba, S. G., Moore, S. D., Tallent, M. K., and G. R. Siggins. (2003). Ethanol increases GABAergic transmission at both pre- and post-synaptic sites in rat central amygdala neurons. *Proc Natl Acad Sci USA* 100: 2053-2058.
59. Sambrook, K. J., Fritsch, E. F. and T. Maniatis. Molecular Cloning a Laboratory Manual. Cold Spring Harbor Press. Plainview, N.Y. 1989.
60. Saxena, N. C., Neelands, T. R. and R. L. Macdonald. 1997. *Mol. Pharmacol.* 51: 328-335.
61. Saxena, N. C. and R. L. Macdonald. 2001. *J. Neurosci.* 14, 7077-7086.
62. Seeburg, P. H. et al. 1990. The GABAA receptor family: molecular and functional diversity. *Cold Spring Harb. Symp. Quant. Biol.* 55: 29-40.
63. Shivers, B. D. et al. 1989. Two novel GABAA receptor subunits exist in distinct neuronal subpopulations. *Neuron* 3: 327-337.
64. Smith, S. S., Gong, Q. H., Hsu, F. C., Markowitz, R. S., Ffrench-Mullen, J. M. H., and X. Li. 1998a. GABAA receptor a subunit suppression prevents withdrawal properties of an endogenous steroid. *Nature* 392: 926-929.
65. Smith, S. S., Gong, Q. H., Li, X., Moran, M. H., Bitran, D., Frye, C. A., and F. C. Hsu. 1998b. Withdrawal from 3 a OH-5 a pregnan-20-one withdrawal using a pseudopregnancy model alters the kinetics of hippocampal GABAA-gated current and increases the GABAA receptor a subunit in association with increased anxiety. *J. Neurosci.* 18: 5275-5284.
66. Sundstrom, I., Nyberg, S., and T. Backstrom. 1997. Patients with premenstrual syndrome have reduced sensitivity to midazolam compared to control subjects. *Neuropsychopharmacology* 17: 370-381.
67. Sundstrom-Poromaa, I., Smith, D. H., Gong, Q., Sabado, T. N., Li, X., Light, A., Wiedmann, M., Williams, K., and S. Smith. 2002. Hormonally regulated a b d GABAA receptors are a target for alcohol. *Nat. Neurosci.* 5: 721-722.
68. Sur, C. et al. 1999. *Mol. Pharmacol.* 56: 110-115.
69. Towbin, H., Staehelin, T. & J. Gordon. 1979. *Proc. Natl. Acad. Sci.* 76: 4350-4354.
70. Tyndale, R. F., Hales, T. G., Olsen, R. W. and A. J. Tobin. 1994. *J. Neurosci.* 14: 5417-5428.
71. Ueno, S., et al. 2001. *Alcohol Clin. Exp. Res.* 25: 76S-81S.
72. Van Doren, M. J., Matthews, D. B., Janis, G. C., Grobin, A. C., Devaud, L. L., and A. L. Morrow. 2000. Neuroactive steroid 3alpha-hydroxy-5alpha-pregnan-20-one modulates electrophysiological and behavioral actions of ethanol. *J. Neurosci.* 20:1982-1989.
73. van Erp, A. M., and K. A. Miczek. 2001. Persistent suppression of ethanol self-administration by brief social stress in rats and increased startle response as index of withdrawal. *Physiol Behav* 73: 301-311.
74. Wallner, M., Hanchar, H. J. and R. W. Olsen, (2003). Ethanol enhances alpha4-beta3-delta and alpha6-beta3-delta gamma-aminobutyric acid type A receptors at low concentrations known to affect humans. *Proc Nat Acad Sci* 100: 15218-15223.
75. Wafford, K. A., Thompson, S. A., Sikela, J., Wilcox, A. S., and P. J. Whiting. 1996. Functional characterization of human GABA receptors containing the α subunit. *Mol. Pharmacol.* 50:670-678.
76. Wan, F. J., Berton, F., Madamba, S. G., Francesconi, W. and G. R. Siggins. 1996. *Proc. Natl. Acad. Sci. USA* 93: 5049-5054.
77. Wiedmann, B., Sakai, H., Davis, T. S. and M. Wiedmann. 1994. *Nature* 370, 434-440.
78. Williams, K., Russell, S. L., Shen, Y. M., and P. B. Molinoff. 1993 *Neuron* 10:267-278.
79. Williams, K. 1993. *Mol. Pharmacol.* 44: 851-859.

80. Wisden, W., Laurie, D. J., Monyer, H., and P. Seeburg. 1991. Cloning, pharmacological characteristics and expression pattern of the rat GABAA receptor a subunit. *FEBS Lett.* 289: 227-230.

81. Wisden, W., Laurie, D. J., Monyer, H., and P. Seeburg. 1992. The distribution of 13 GABA-A receptor subunit mRNAs in the rat brain. I. Telencephalon, diencephalon, mesencephalon. *J. Neurosci.* 12:1040-1062.

82. Wisor, J. P., Delorey, T. M., Homanics, G. E. and D. M. Edgar. 2002. Sleep States and Sleep Electroencephalographic Spectral Power in Mice Lacking the Beta 3 subunit or the GABA(A) receptor. *Brain Res.* 955:221-228.

83. Ymer, S. et al. 1989. GABA(A) receptor beta subunit heterogeneity: Functional Expression of Cloned cDNAs. *EMBO J.* 8:1655-1670.

84. Yu, R., and M. K. Ticku. 1995. Chronic neurosteroid treatment decreases the efficacy of benzodiazepine ligands and neurosteroids at the GABAA receptor complex in mammalian cortical neurons. *JPET* 275:784-789.

85. Zhang, W. N., Bast, T. and J. Feldon. 2000. *Neuroscience* 101, 589-599.

What is claimed is:

1. A method of screening for a drug which decreases expression of the $\alpha_4\beta_2\delta$ GABA$_A$ receptor, said method comprising: (a) expressing $\alpha_4$, $\beta_2$ and $\delta$ subunits of the GABA$_A$ receptor in cultured eukaryotic cells; (b) applying a drug to the cultured eukaryotic cells of (a); (c) measuring the levels of the $\delta$ subunit of said GABA$_A$ receptor from the treated cultured eukaryotic cells of step (b); (d) determining whether the drug applied in step (b) decreases expression of said $\delta$ subunit of said GABA$_A$ receptor; and (e) correlating a decrease in expression of said $\delta$ subunit of the GABA$_A$ receptor found in the treated cultured eukaryotic cells of step (b) when compared to control cultured eukaryotic cells expressing $\alpha_4$, $\beta_2$, and $\delta$ subunits of the GABA$_A$ receptor having no drug application, with the identification of a drug which decreases expression of the $\alpha_4\beta_2\delta$ GABA$_A$ receptor.

* * * * *